US011131622B2

(12) United States Patent
Umetsu et al.

(10) Patent No.: US 11,131,622 B2
(45) Date of Patent: Sep. 28, 2021

(54) INFORMATION PROCESSING DEVICE, INFORMATION PROCESSING METHOD, AND INFORMATION PROCESSING SYSTEM

(71) Applicant: SONY CORPORATION, Tokyo (JP)

(72) Inventors: Tomoyuki Umetsu, Tokyo (JP); Yasunobu Kato, Kanagawa (JP); Nobuhiro Hayashi, Kanagawa (JP); Naoki Ide, Tokyo (JP)

(73) Assignee: SONY CORPORATION, Tokyo (JP)

( * ) Notice: Subject to any disclaimer, the term of this patent is extended or adjusted under 35 U.S.C. 154(b) by 281 days.

(21) Appl. No.: 16/097,297

(22) PCT Filed: Feb. 10, 2017

(86) PCT No.: PCT/JP2017/004913
§ 371 (c)(1),
(2) Date: Oct. 29, 2018

(87) PCT Pub. No.: WO2017/191699
PCT Pub. Date: Nov. 9, 2017

(65) Prior Publication Data
US 2019/0137383 A1 May 9, 2019

(30) Foreign Application Priority Data

May 6, 2016 (JP) .............................. JP2016-093353

(51) Int. Cl.
*G01N 21/27* (2006.01)
*G16C 20/30* (2019.01)
(Continued)

(52) U.S. Cl.
CPC ......... *G01N 21/27* (2013.01); *G01N 15/1012* (2013.01); *G01N 15/1429* (2013.01);
(Continued)

(58) Field of Classification Search
CPC .............. G01N 21/27; G01N 15/1012; G01N 15/1429; G01N 21/17; G01N 21/64; G01N 2015/1006; G16C 20/30
(Continued)

(56) References Cited

U.S. PATENT DOCUMENTS

2010/0112727 A1 5/2010 Todd et al.
2013/0026391 A1* 1/2013 Sekino ............... G01N 21/6458
250/459.1
(Continued)

FOREIGN PATENT DOCUMENTS

CN 102216778 A 10/2011
CN 102901693 A 1/2013
(Continued)

OTHER PUBLICATIONS

Office Action for JP Patent Application No. 2018-515392, dated Aug. 18, 2020, 03 pages of Office Action and 03 pages of English Translation.
(Continued)

*Primary Examiner* — Michael P Nghiem
(74) *Attorney, Agent, or Firm* — Chip Law Group

(57) ABSTRACT

An information processing device includes a statistical processing unit that performs statistical processing for a group of spectra obtained by applying light to a group of microparticles that exhibit one response property with respect to light, and on a basis of a result of the statistical processing, exclude a spectrum indicating an outlier from the group of spectra, and a reference spectrum calculation unit that calculates a reference spectrum using the group of spectra from which the spectrum indicating the outlier has been excluded.

17 Claims, 19 Drawing Sheets

(51) Int. Cl.
*G01N 21/64* (2006.01)
*G01N 21/17* (2006.01)
*G01N 15/14* (2006.01)
*G01N 15/10* (2006.01)

(52) U.S. Cl.
CPC ......... *G01N 15/1459* (2013.01); *G01N 21/17* (2013.01); *G01N 21/64* (2013.01); *G16C 20/30* (2019.02); *G01N 2015/1006* (2013.01)

(58) Field of Classification Search
USPC .......................................................... 702/32
See application file for complete search history.

(56) References Cited

U.S. PATENT DOCUMENTS

2013/0323825 A1* 12/2013 Sekino ............... G01N 21/6486
435/287.2
2017/0059409 A1* 3/2017 Eom ....................... G01J 3/027

FOREIGN PATENT DOCUMENTS

| EP | 2998725 A1 | 3/2016 |
|---|---|---|
| JP | 08-145891 A | 6/1996 |
| JP | 2003-098077 A | 4/2003 |
| JP | 007-240424 A | 9/2007 |
| JP | 2007-240424 A | 9/2007 |
| JP | 2010-110567 A | 5/2010 |
| JP | 2012-503202 A | 2/2012 |
| JP | 2013-024792 A | 2/2013 |
| KR | 10-2011-0084190 A | 7/2011 |
| WO | 2010/033838 A1 | 3/2010 |
| WO | 2014/196363 A1 | 12/2014 |

OTHER PUBLICATIONS

International Search Report and Written Opinion of PCT Application No. PCT/JP2017/004913, dated Apr. 18, 2017, 09 pages of ISRWO.

* cited by examiner

| Marker | Fluorochrome |
|---|---|
| CD1 | FITC |
| CD2 | PE |
| ⋮ | ⋮ |
| Neg | Negative |

INFORMATION PROCESSING DEVICE, INFORMATION PROCESSING METHOD, AND INFORMATION PROCESSING SYSTEM

CROSS REFERENCE TO RELATED APPLICATIONS

This application is a U.S. National Phase of International Patent Application No. PCT/JP2017/004913 filed on Feb. 10, 2017, which claims priority benefit of Japanese Patent Application No. JP 2016-093353 filed in the Japan Patent Office on May 6, 2016. Each of the above-referenced applications is hereby incorporated herein by reference in its entirety.

TECHNICAL FIELD

The present disclosure relates to an information processing device, an information processing method, a program, and an information processing system.

BACKGROUND ART

In order to analyze properties that microparticles such as cells, microorganisms, liposomes, or the like have, an analysis approach by means of an apparatus (such as a flow cytometer, for example) that measures the intensity, spectrum, and the like of fluorescence or scattered light emitted from the microparticles is used. For example, in flow cytometry, excitation light such as laser light is applied to microparticles flowing in a channel, and fluorescence, scattered light, or the like emitted from the microparticles is detected by photodetectors such as a plurality of photo multiplier tubes (PMTs). The detected light is quantified by being converted into an electric signal. By performing statistical processing for this quantified data, the above-described properties of microparticles are analyzed.

For fluorescence detection in a flow cytometer, there is also a method of measuring the intensity of light in continuous wavelength ranges as a spectrum, besides a method of selecting a plurality of rays of light in discontinuous wavelength ranges using wavelength selection elements such as filters to measure the intensity of light in each of the wavelength ranges. For example, Patent Literature 1 below discloses a technology of deconvoluting spectra obtained by applying laser light to microparticles labeled using a plurality of fluorochromes by a spectrum (reference spectrum) per fluorochrome to analyze the fluorescence intensity per light-emitting element such as a fluorochrome that labels the microparticles. According to such a technology, the measured spectrum can be expressed by a linear sum obtained by multiplying the reference spectrum per light-emitting element by a predetermined coefficient. Accordingly, the fluorescence intensity of each fluorochrome that labels the microparticles can be calculated.

CITATION LIST

Patent Literature

Patent Literature 1: JP 2013-24792A

DISCLOSURE OF INVENTION

Technical Problem

In order to sufficiently ensure the calculation accuracy of the fluorescence intensity per light-emitting element, it is required that the accuracy of the reference spectrum for use in the above-described deconvolution is sufficiently high. Since the shape of fluorescence spectra acquired from microparticles affects a measurement environment, the above-described reference spectrum is usually generated on the basis of spectra obtained from microparticles simply stained with one fluorochrome (or unstained) in an environment identical to the measurement environment. However, depending on the measurement environment or microparticles, many noises or abnormal values may be included in the generated reference spectrum. When noises or abnormal values are included in the reference spectrum, the accuracy of the reference spectrum is reduced, and thus, the calculation accuracy of the fluorescence intensity per light-emitting element calculated using the reference spectrum can be reduced.

Therefore, the present disclosure proposes an information processing device, an information processing method, a program, and an information processing system being novel and improved that can increase the accuracy of a reference spectrum.

SUMMARY

According to the present disclosure, there is provided an information processing device including: a statistical processing unit configured to perform statistical processing for a group of spectra obtained by applying light to a group of microparticles that exhibit one response property with respect to light, and on a basis of a result of the statistical processing, exclude a spectrum indicating an outlier from the group of spectra; and a reference spectrum calculation unit configured to calculate a reference spectrum using the group of spectra from which the spectrum indicating the outlier has been excluded.

In addition, according to the present disclosure, there is provided an information processing method including, by a processor: performing statistical processing for a group of spectra obtained by applying light to a group of microparticles that exhibit one response property with respect to light, and on a basis of a result of the statistical processing, excluding a spectrum indicating an outlier from the group of spectra; and calculating a reference spectrum using at least one group of spectra from which the spectrum indicating the outlier has been excluded.

In addition, according to the present disclosure, there is provided a program for causing a computer to function as: a statistical processing unit configured to perform statistical processing for a group of spectra obtained by applying light to a group of microparticles that exhibit one response property with respect to light, and on a basis of a result of the statistical processing, exclude a spectrum indicating an outlier from the group of spectra; and a reference spectrum calculation unit configured to calculate a reference spectrum using at least one group of spectra from which the spectrum indicating the outlier has been excluded.

In addition, according to the present disclosure, there is provided an information processing system including: a measurement device including a measurement unit configured to apply light to a measurement target to measure a spectrum related to light emission of the measurement target; and an information processing device including an information processing device including a statistical processing unit configured to perform statistical processing for a group of spectra related to a group of microparticles that exhibit one response property with respect to light, obtained from the measurement unit, and on a basis of a result of the statistical processing, exclude a spectrum indicating an outlier from the group of spectra, and a reference spectrum calculation unit configured to calculate a reference spectrum using at least one group of spectra from which the spectrum indicating the outlier has been excluded.

Advantageous Effects of Invention

According to the present disclosure as described above, it is possible to increase the accuracy of a reference spectrum.

Note that the effects described above are not necessarily limitative. With or in the place of the above effects, there may be achieved any one of the effects described in this specification or other effects that may be grasped from this specification.

DETAILED DESCRIPTION

Figure 1:
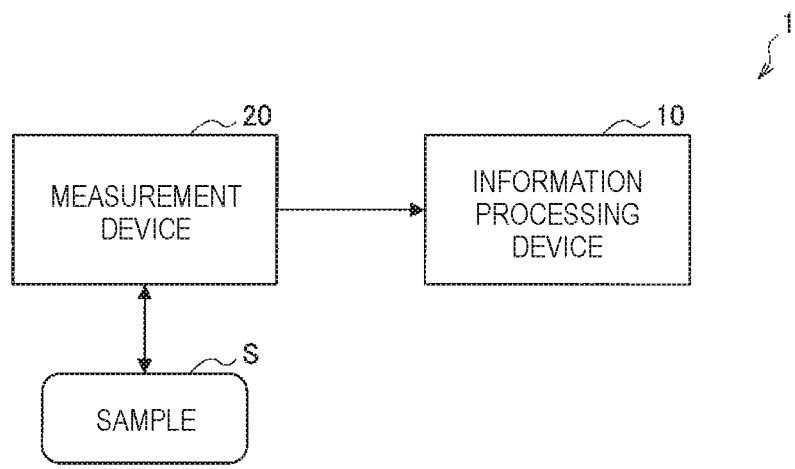
FIG. 1 is a diagram showing a schematic configuration of an information processing system according to one embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Overview of information processing system
1.1. Configuration of information processing system
1.2. Configuration of information processing device
1.3. As to generation of reference spectrum
2. First embodiment (generation of reference spectrum corresponding to fluorochrome)
2.1. Configuration of reference spectrum generation unit
2.2. Flow of processing in reference spectrum generation unit
2.3. Effects
3. Second embodiment (generation of reference spectrum related to autofluorescence)
3.1. Flow of processing in reference spectrum generation unit
3.2. Application example
4. Hardware configuration example
5. Conclusion 1. Overview of Information Processing System 1.1. Configuration of Information Processing System FIG. 1 is a diagram showing a schematic configuration of an information processing system 1 according to one embodiment of the present disclosure. As shown in FIG. 1, the information processing system 1 includes an information processing device 10 and a measurement device 20 that measures a spectrum corresponding to a sample S. The information processing device 10 and the measurement device 20 are connected with wired or wireless various networks.

As a microparticle which is the sample S in the present embodiment, a bio-related microparticle such as a cell, a microorganism, or a liposome, a synthetic particle such as a latex particle, a gel particle, an industrial particle, or a microbead, or the like, for example, can be utilized.

The bio-related microparticle includes chromosomes, liposomes, mitochondria, organelles, and the like included in various cells. The cell includes animal cells (such as haematopoietic cells) and plant cells. The microorganism includes bacteria such as *Escherichia coli*, viruses such as tobacco mosaic virus, fungi such as yeast cells, and the like. In addition, the bio-related microparticle may include bio-related polymers such as nucleic acid, proteins such as enzyme, their composites, and the like.

In addition, the industrial particle may be an organic polymer material, an inorganic polymer material, metal, or the like, for example. For example, the organic polymer material includes polystyrene, styrene-divinylbenzene, polymethylmethacrylate, and the like. The inorganic polymer material includes glass, silica, magnetic substance materials, and the like. The metal includes noble metal colloid, aluminum, and the like. In addition, the shape of these microparticles is mainly spherical, but may be non-spherical. In addition, the size, mass, and the like of the microparticles are not particularly limited.

The information processing device 10 acquires measured data of the sample S measured by the measurement device 20, separates (deconvolutes) a spectrum which is the acquired measured data into a plurality of spectra, and analyzes the intensity of each of the separated spectra. For example, the information processing device 10 separates an acquired fluorescence spectrum of the sample S into fluorescence spectra derived from a plurality of fluorochromes that label the sample S, and analyzes the amount of fluorescence of each of the separated fluorescence spectra. On the basis of this amount of fluorescence, properties that labeled microparticles have can be analyzed.

Note that the example shown in FIG. 1 illustrates the case where the information processing device 10 according to the present embodiment is provided as a device different from the measurement device 20, whilst the functions of the information processing device 10 according to the present embodiment may be mounted on a computer that controls the operation of the measurement device 20, or may be mounted on any computer provided within an enclosure of the measurement device 20. Note that a detailed configuration of the information processing device 10 will be described in detail in a later stage.

The measurement device 20 applies laser light to the sample S, detects fluorescence, phosphorescence, or scattered light from the sample S, and measures a spectrum corresponding to the sample S from the result of detection of these types of light. That is, the measurement device 20 has the function as a measurement unit. The measurement device 20 according to the present embodiment may measure an emission spectrum, a scattering spectrum, or an absorption spectrum of the sample S, or may measure at least two or more of the emission spectrum, scattering spectrum, and absorption spectrum.

Note that a detailed description of the present technology will be provided below assuming that the measurement device 20 is a flow cytometer that measures a fluorescence spectrum of the sample S.

Before describing the measurement device 20, a microparticle which is a measurement sample in the information processing system 1 according to the present embodiment will be described. The microparticle according to the present embodiment may be labeled with one or more fluorochromes prior to measurement of the fluorescence spectrum, for example. Labeling the microparticle with a plurality of fluorochromes will also be referred to as multiple staining. Labeling the microparticle with fluorochromes can be performed by any publicly-known approach. In the case where the microparticle is a cell, for example, by mixing a fluorescence-labeled antibody against a cell surface molecule and the cell, the antibody is bound to the cell surface molecule. The fluorescence-labeled antibody may be obtained by directly binding a fluorochrome to the antibody, or may be obtained by binding a fluorochrome bound with avidin to a biotin-labeled antibody through an avidin-biotin reaction. In addition, the antibody may be a monoclonal antibody or polyclonal antibody.

For the fluorochromes for multiple labeling of the microparticle, two or more publicly-known substances can be used in combination. As the fluorochromes, for example, phycoerythrin (PE), FITC, PE-Cy5, PE-Cy7, PE-Texas red, allophycocyanin (APC), APC-Cy7, Ethidium bromide, Propidium iodide, Hoechst 33258/33342, DAPI, Acridine orange, Chromomycin, Mithramycin, Olivomycin, Pyronin Y, Thiazole orange, Rhodamine 101 isothiocyanate, BCECF, BCECF-AM, C.SNARF-1, C.SNARF-1-AMA, Aequorin, Indo-1, Indo-1-AM, Fluo-3, Fluo-3-AM, Fura-2, Fura-2-AM, Oxonol, Texas red, Rhodamine 123, 10-N-nonyl-Acridine orange, Fluorecein, Fluorescein diacetate, Carboxyfluorescein, Caboxyfluorescein diacetate, Carboxydichlorofluorescein, Carboxydichlorofluorescein diacetate, and the like can be utilized. As a matter of course, the fluorochromes that can be used in the present embodiment are not limited to the above-described examples.

Figure 2:
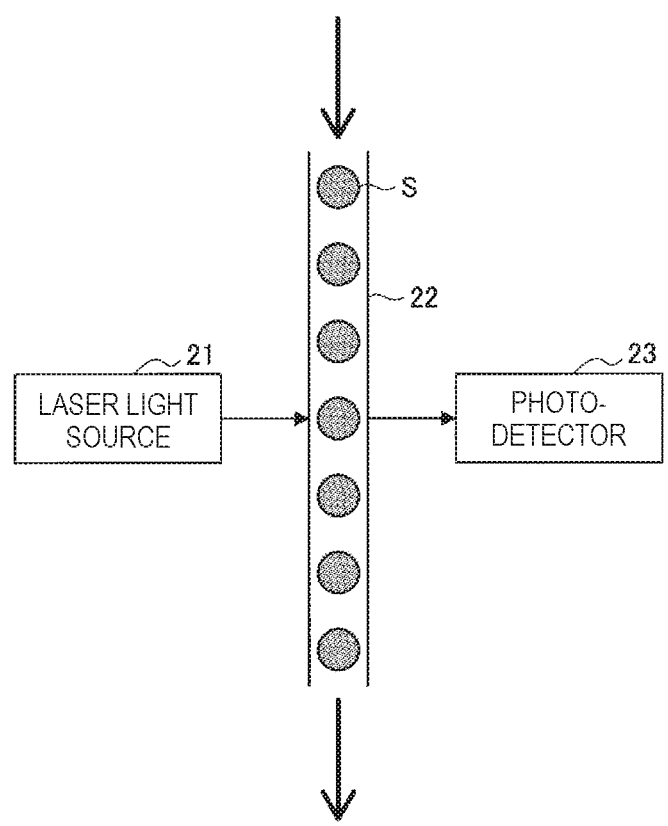
FIG. 2 is a diagram showing a schematic configuration of a flow cytometer which is an example of a measurement device.
Figure 3:
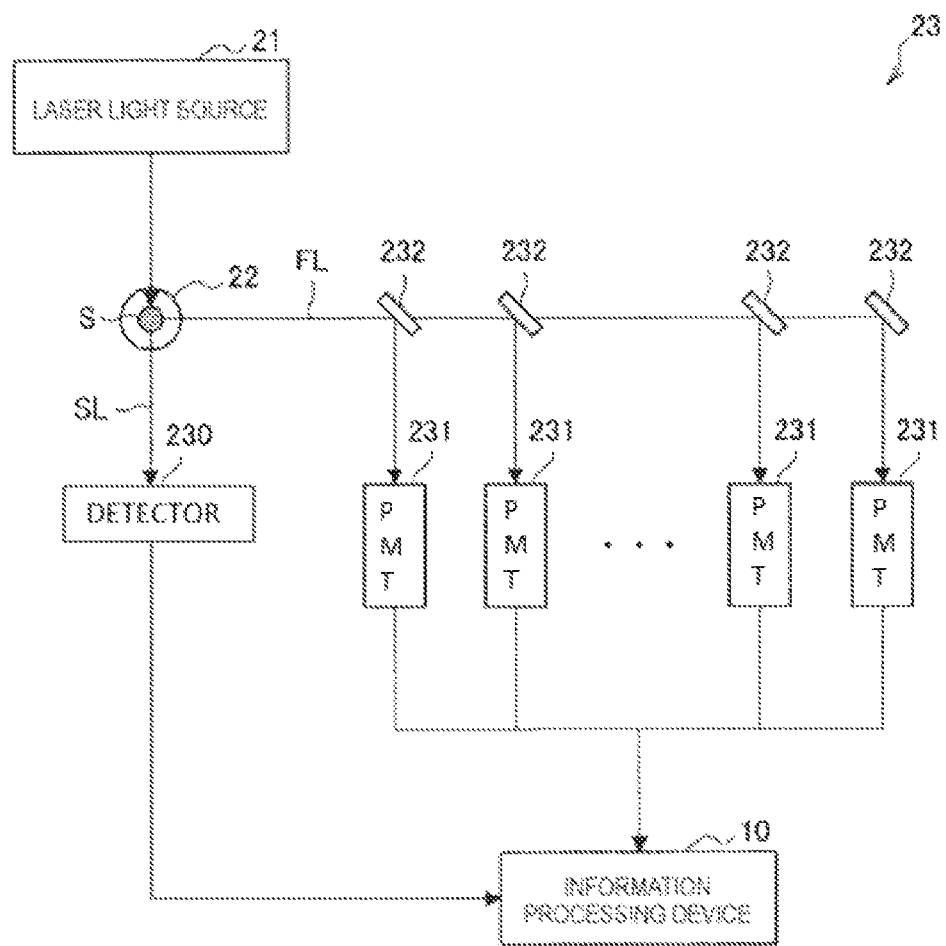
FIG. 3 is a diagram showing an example of a detailed configuration of the flow cytometer.

Next, a configuration of the measurement device 20 will be described. FIG. 2 is a diagram showing a schematic configuration of a flow cytometer which is an example of the measurement device. In addition, FIG. 3 is a diagram showing an example of a detailed configuration of the flow cytometer. The flow cytometer shown in FIG. 2 and FIG. 3 includes a laser light source 21, a microchannel 22, and a photodetector 23.

Referring to FIG. 2, in the flow cytometer, laser light having a wavelength that can excite fluorochromes that may be utilized for staining of the microparticles S is output from the laser light source 21 to the simply-stained, multi-stained, or unstained microparticles S flowing through the microchannel 22. The photodetector 23 detects fluorescence, scattered light, or the like emitted from the microparticles S to which the laser light has been applied. In addition, although not shown in FIG. 2 and FIG. 3, an optical system such as a lens for guiding the laser light to the microparticles S and an optical system for guiding fluorescence, scattered light, or the like emitted from the microparticles S to the photodetector 23 are provided in the flow cytometer.

The laser light source 21 may output laser light of a predetermined wavelength (for example, a wavelength λ=405 nm, 488 nm, 532 nm, 633 nm). In addition, although only a single laser light source 21 is depicted in the example of FIG. 2 and FIG. 3, a plurality of laser light sources may be provided.

The microchannel 22 is provided to cause the microparticles S to flow in line in a flow direction. A publicly-known microchannel chip or the like is used as the microchannel 22.

In addition, as shown in FIG. 3, the photodetector 23 includes a detector 230, a photomultiplier (PMT) 231, and a dichroic mirror 232 (an example of an optical filter).

The detector 230 is a device for detecting scattered light SL emitted from the microparticle S. The detector 230 is implemented by, for example, a charge coupled device (CCD), complementary metal oxide semiconductor (CMOS), photodiode, or the like. Measured data of the scattered light SL detected by the detector 230 may be output to the information processing device 10 according to the present embodiment.

The PMT 231 is a device for detecting fluorescence FL emitted from the microparticle S. A plurality of the PMTs 231 are provided as shown in FIG. 3. The fluorescence FL emitted from the microparticles S resulting from the laser light output from the laser light source 21 is dispersed by the dichroic mirrors 232 provided between the microchannel 22 and the PMTs 231, and guided to the respective PMTs 231.

Note that the number of the PMTs 231 installed is set as appropriate in accordance with the distribution of response properties (for example, fluorescence spectra corresponding to fluorochromes) or the like with respect to light that fluorochromes or microparticles which will be described later have. By integrating measured data detected by the respective PMTs 231, the fluorescence spectra of the microparticles S are obtained. The PMTs 231 output measured data indicating the result of detection of the fluorescence FL of a corresponding wavelength band to the information processing device 10 according to the present embodiment.

As described above, the information processing device 10 according to the present embodiment obtains fluorescence spectra obtained by continuously observing fluorescence from the microparticles S. Note that the flow cytometer shown in FIG. 3 is provided with a series of optical systems for sensing scattered light from the microparticles S, whilst such optical systems may not be provided. In addition, the flow cytometer shown in FIG. 3 disperses the fluorescence FL discharged from the microparticles S by the dichroic mirrors 232 for guide to the PMTs 231, whilst the fluorescence FL discharged from the microparticles S may be separated into fluorescence having wavelengths included in a plurality of specific wavelength bands by a plurality of wavelength selection filters such as bandpass filters. In addition, the above-described flow cytometer may disperse the fluorescence FL discharged from the microparticles S using a spectrometer such as a prism. That is, some structural elements may be deformed in any manner as long as it is configured such that fluorescence spectra obtained by exciting the microparticles S with laser light can be selectively measured per predetermined wavelength band, and the result of measurement can be input to the information processing device 10.

An example of the measurement device 20 according to the present embodiment has been described above.

1.2. Configuration of Information Processing Device

Figure 4:
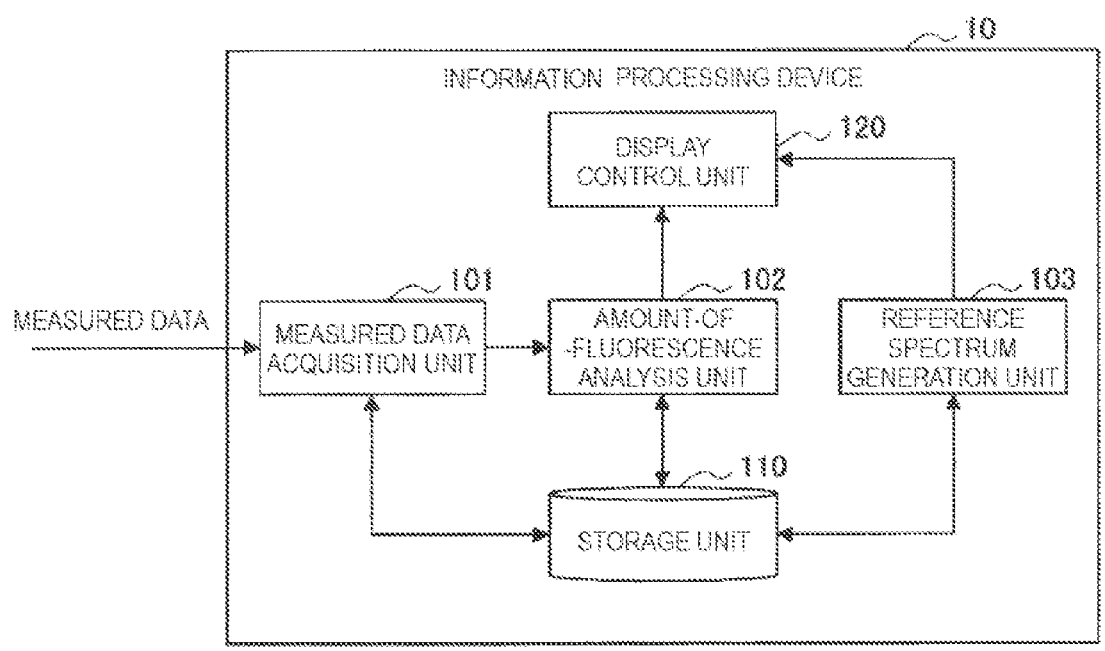
FIG. 4 is a functional block diagram showing an example of a functional configuration of an information processing device according to the embodiment.

Next, a configuration of the information processing device 10 according to one embodiment of the present disclosure will be described with reference to FIG. 4 and FIG. 5. FIG. 4 is a functional block diagram showing an example of a functional configuration of the information processing device 10 according to one embodiment of the present disclosure.

As shown in FIG. 4, the information processing device 10 according to the present embodiment includes a measured data acquisition unit 101, an amount-of-fluorescence analysis unit 102, a reference spectrum generation unit 103, a storage unit 110, and a display control unit 120.

(Measured Data Acquisition Unit)

The measured data acquisition unit 101 acquires measured data generated by the measurement device 20 from the measurement device 20. Here, measured data of the microparticles S acquired from the measurement device 20 is, for example, data representing the intensity of a spectrum generated by applying laser light to one or more microparticles S. In spectrum measurement for one or more microparticles S, a time slot exists although being minute. Thus, the accumulation intensity, maximum intensity, average intensity, or the like in the minute time slot, for example, is used for measured data according to the present embodiment.

The measured data acquisition unit 101 stores the acquired measured data in the storage unit 110. On this occasion, the measured data acquisition unit 101 may store the acquired measured data in the storage unit 110 in association with time information such as the date and time when the measured data is acquired, information related to a measurement condition of the measurement device 20, or the like. In addition, the measured data acquisition unit 101 may output the measured data directly to the amount-of-fluorescence analysis unit 102 for real-time analysis.

(Amount-of-Fluorescence Analysis Unit)

The amount-of-fluorescence analysis unit 102 separates the fluorescence spectrum related to measured data acquired from the measured data acquisition unit 101 or the storage unit 110 into spectra of respective fluorochromes that label the microparticles S (and autofluorescence spectra derived from the microparticles S), and analyzes the amount of fluorescence from the intensity per separated spectrum. For separating the fluorescence spectrum, a reference spectrum is used. The reference spectrum is a spectrum obtained by measuring and standardizing a simply-stained sample simply stained with each fluorochrome. This reference spectrum is generated by the reference spectrum generation unit 103.

The amount-of-fluorescence analysis unit 102 analyzes the amount of fluorescence of each fluorochrome by fitting the reference spectrum of each fluorochrome used for multiple staining of the microparticles S into fluorescence spectra related to measured data of the microparticles S. Fitting of the reference spectrum is performed by any publicly-known approach such as the least squares method.

Figure 5:
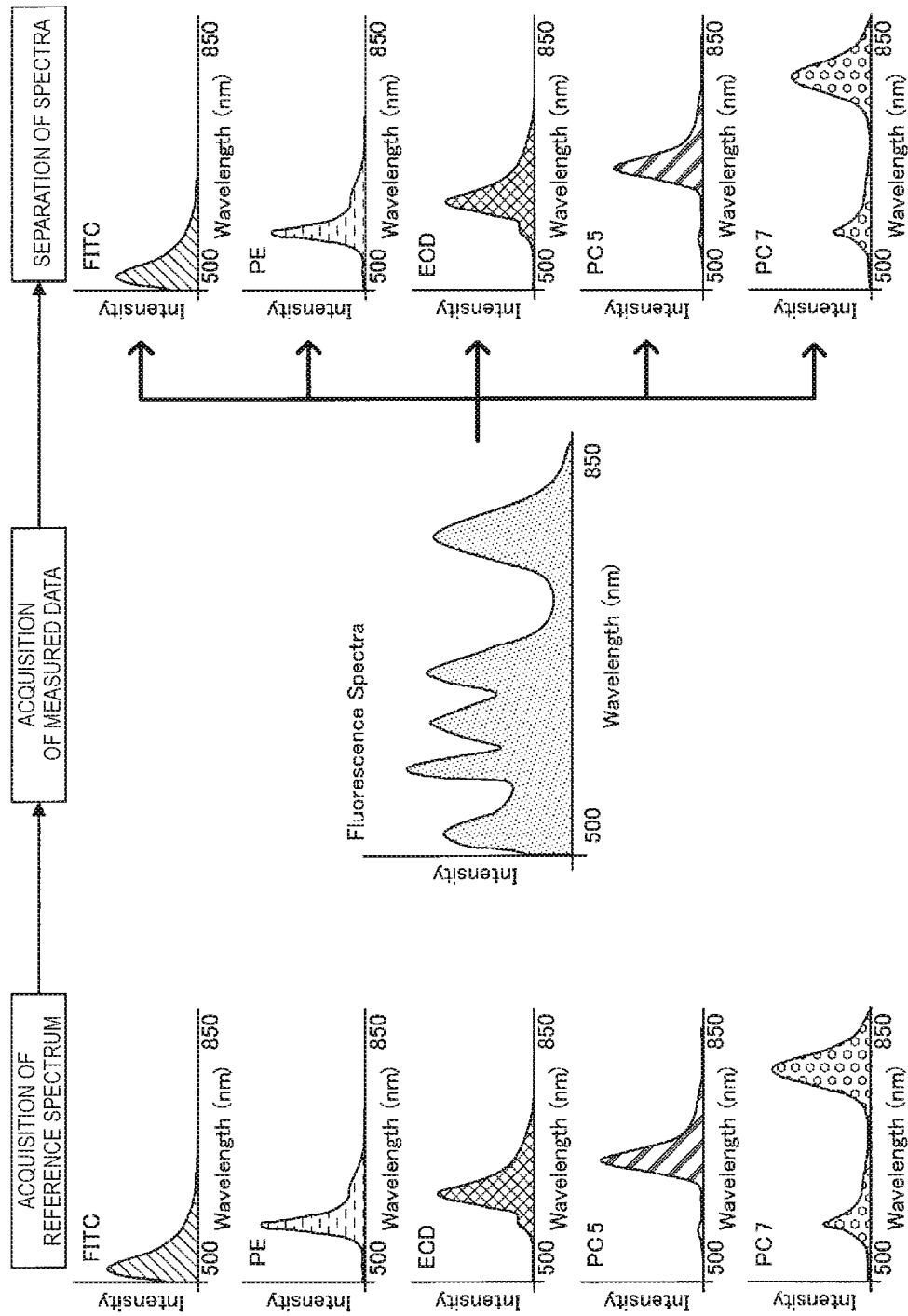
FIG. 5 is a diagram for describing amount-of-fluorescence analysis processing performed by an amount-of-fluorescence analysis unit according to the embodiment.

With reference to FIG. 5, amount-of-fluorescence analysis processing performed by the amount-of-fluorescence analysis unit 102 will be described. FIG. 5 is a diagram for describing the amount-of-fluorescence analysis processing performed by the amount-of-fluorescence analysis unit 102 according to the present embodiment.

The amount-of-fluorescence analysis unit 102 first selects a fluorochrome that labels the microparticle S by a user operation or the like, and acquires the reference spectrum of the fluorochrome from the storage unit 110. In the example shown in FIG. 5, reference spectra of five types of fluorochromes: FITC; PE; ECD; PC5; and PC7 are shown.

Next, the amount-of-fluorescence analysis unit 102 acquires measured data of the microparticles S labeled with the above-described fluorochromes and the reference spectrum corresponding to each fluorochrome from the storage unit 110, and separates fluorescence spectra related to the measured data per fluorochrome. The fluorescence spectra shown in FIG. 5 are superimposed reference spectra of the fluorochromes used for labeling. That is, the amount-of-fluorescence analysis unit 102 analyzes the fluorescence intensity of each reference spectrum by fitting each reference spectrum into the fluorescence spectra. Fluorescence spectra resulting from the respective fluorochromes obtained by fitting are as shown in FIG. 5. The reference spectrum and the fluorescence spectrum of each fluorochrome after fitting are identical in shape, whilst the intensity of the fluorescence spectrum is changed by weighting in fitting. The intensity corresponds to the amount of fluorescence of each fluorochrome.

The amount-of-fluorescence analysis unit 102 analyzes the amount of fluorescence of each fluorochrome from the intensity of each fluorescence spectrum. Accordingly, the degree of the amount of fluorescence of the fluorochromes included in the microparticles S can be learned.

In addition, the amount-of-fluorescence analysis unit 102 may separate the fluorescence spectra related to the measured data using the approach disclosed in Patent Literature 1 above (JP 2013-24792A1), for example, and analyze the amount of fluorescence of each fluorochrome.

Note that the amount-of-fluorescence analysis unit 102 is also capable of analyzing the amount of fluorescence of autofluorescence spectra obtained from unstained microparticles.

The amount-of-fluorescence analysis unit 102 stores data related to the analysis result in the storage unit 110. On this occasion, the amount-of-fluorescence analysis unit 102 may store the data related to the analysis result in the storage unit 110 in association with time information such as the date and time when the data is generated, information related to measured data, or the like. In addition, the amount-of-fluorescence analysis unit 102 may output the analysis result to the display control unit 120. A screen related to the analysis result is presented to a user by the display control unit 120.

In addition, the amount-of-fluorescence analysis unit 102 may present the analysis result to the user as a printed material via an output device such as a printer, or may output data related to the analysis result to various recording media such as a CD, a DVD, a Blu-ray (registered trademark) disc, a USB memory, or an external HDD (Hard Disk Drive), and the like. In addition, the amount-of-fluorescence analysis unit 102 may output data related to the analysis result to an external device with which the information processing device 10 according to the present embodiment is capable of communicating via various communication networks.

(Reference Spectrum Calculation Unit)

The reference spectrum generation unit 103 generates a reference spectrum on the basis of the fluorescence spectra related to measured data of unstained microparticles or microparticles labeled with at least one fluorochrome, acquired from the storage unit 110. The reference spectrum is a spectrum for reference for analyzing the amount of fluorescence of fluorochromes used for labeling the microparticles from one fluorescence spectrum by the amount-of-fluorescence analysis unit 102, as described above.

For example, the reference spectrum generation unit 103 performs the following processing when calculating the reference spectrum of one fluorochrome. Specifically, the reference spectrum generation unit 103 first acquires measured data of microparticles labeled only with one fluorochrome and measured data of unstained microparticles from the storage unit 110. By performing statistical processing for these pieces of measured data, the reference spectrum generation unit 103 calculates the reference spectrum of the one fluorochrome. In addition, by performing statistical processing only for the measured data of unstained microparticles, the reference spectrum generation unit 103 may calculate the reference spectrum related to autofluorescence spectra of the microparticles.

The reference spectrum generation unit 103 stores data related to the reference spectrum in the storage unit 110. On this occasion, the reference spectrum generation unit 103 may store the data related to the reference spectrum in the storage unit 110 in association with time information such as the date and time when the data is generated, information related to measured data, or the like. In addition, the reference spectrum generation unit 103 may output the data related to the reference spectrum to the display control unit 120. The data related to the reference spectrum is presented to the user by the display control unit 120.

Note that a detailed configuration of the reference spectrum generation unit 103 according to the present embodiment will be described later.

(Storage Unit)

The storage unit 110 is storage means that the information processing device 10 includes, and stores information obtained by each functional unit that the information processing device 10 has, and the like. In addition, the storage unit 110 outputs stored information as appropriate in accordance with a request from each functional unit that the information processing device 10 has. Measured data acquired by the measured data acquisition unit 101, data related to the analysis result analyzed by the amount-of-fluorescence analysis unit 102, data related to the reference spectrum calculated by the reference spectrum generation unit 103, and the like, for example, may be stored in the storage unit 110. In addition, execution data such as programs corresponding to various applications that the display control unit 120 utilizes for displaying various types of information on a display screen may be stored in the storage unit 110. In addition, various parameters, temporary data, or the like that may occur during processing performed by the information processing device 10 may be stored in the storage unit 110 as appropriate. In addition, the storage unit 110 may be provided with various databases. The various databases may include, for example, a database that stores the above-described measured data, data related to the analysis result, or data related to the reference spectrum. The storage unit 110 is provided so as to allow each functional unit that the information processing device 10 according to the present embodiment has to freely perform reading and writing.

(Display Control Unit)

The display control unit 120 performs display control of a display screen in a display device not shown such as a display that the information processing device 10 includes or a display device such as a display provided external to the information processing device 10. For example, the display control unit 120 may perform display control of the display screen on the basis of data related to the analysis result obtained by the amount-of-fluorescence analysis unit 102. In addition, the display control unit 120 may perform display control of the display screen on the basis of data related to the reference spectrum generated by the reference spectrum generation unit 103. The display control allows the user of the information processing device 10 to learn information about the analysis result or reference spectrum.

1.3. As to Reference Spectrum

The reference spectrum is a spectrum used for analyzing the amount of fluorescence of each fluorochrome in the amount-of-fluorescence analysis unit 102, as described above. In order to analyze the amount of fluorescence of each fluorochrome with high accuracy, the correctness of the shape of the reference spectrum is required.

The reference spectrum generation unit 103 performs processing of generating the reference spectrum of one fluorochrome (or autofluorescence of microparticles) in the following procedure, for example. First, the reference spectrum generation unit 103 acquires measured data of microparticles labeled only with the one fluorochrome and measured data of unstained microparticles from the storage unit 110. Next, the reference spectrum generation unit 103 performs statistical processing (for example, averaging processing) for measured data related to autofluorescence, and obtains a spectrum related to autofluorescence having been averaged (an averaged autofluorescence spectrum).

Then, the reference spectrum generation unit 103 subtracts the above-described averaged autofluorescence spectrum from each of a plurality of fluorescence spectra related to measured data of microparticles labeled only with the above-described one fluorochrome. Next, in order to treat the plurality of fluorescence spectra after subtraction equivalently, the reference spectrum generation unit 103 normalizes a spectrum total sum for each of the plurality of fluorescence spectra. Then, the reference spectrum generation unit 103 averages the normalized spectrum. A spectrum obtained by the averaging will be referred to as an averaged fluorescence spectrum. Then, in order to make the intensity uniform with the reference spectra of other fluorochromes, the reference spectrum generation unit 103 normalizes the intensity of the averaged fluorescence spectrum. Accordingly, the reference spectrum of the above-described one fluorochrome is generated.

Figure 6:
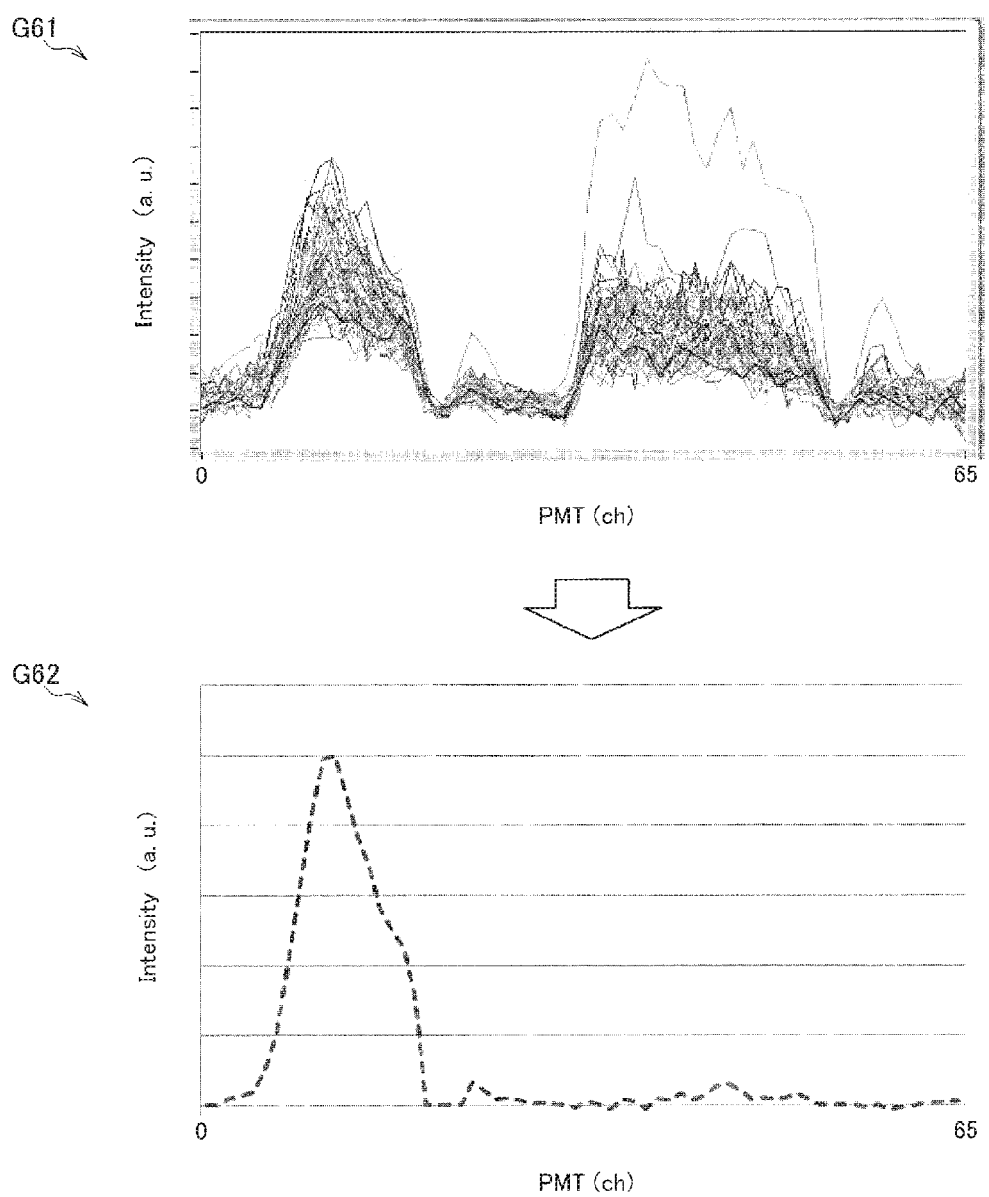
FIG. 6 is a diagram showing an example of a reference spectrum generated by a reference spectrum generation unit.

FIG. 6 is a diagram showing an example of the reference spectrum generated by the reference spectrum generation unit 103. A graph G61 in FIG. 6 shows an example of a plurality of fluorescence spectra related to measured data used for calculation of the reference spectrum, and a graph G62 in FIG. 6 shows an example of the reference spectrum generated by the reference spectrum generation unit 103 on the basis of the plurality of fluorescence spectra shown in the graph G61. Note that the horizontal axis of the graphs representing the spectra shown in the graph G61 and the graph G62 indicates the PMT channel (that is, equivalent to the wavelength), and the vertical axis indicates the intensity of the spectra.

In the spectra shown in the graph G61, peaks observed at 5 ch to 20 ch and peaks observed in the vicinity of 30 ch to 55 ch mainly exist. Among them, the peaks observed at 5 ch to 20 ch are peaks resulting from a fluorochrome A that labels microparticles, and the peaks observed in the vicinity of 30 to 55 ch are peaks resulting from autofluorescence of microparticles.

By subtracting the averaged autofluorescence spectrum calculated separately from each of the fluorescence spectra shown in the graph G61 and averaging and normalizing fluorescence spectra after subtraction, the reference spectrum generation unit 103 generates the reference spectrum shown in the graph G62. If variations in measured data used when generating the reference spectrum are variations of the degree as shown in the graph G61, it is possible to obtain a reference spectrum showing a peak resulting from the fluorochrome A, as shown in the graph G62.

However, depending on variations in measured data to be used for generation of the reference spectrum, it is possible that the accuracy of the generated reference spectrum is reduced. For example, (1) in the case where an abnormal value is included in a spectrum related to measured data, or (2) in the case where fluorescence is weak, and a noise included in a spectrum becomes relatively large, it is considered that the accuracy of the generated reference spectrum may be reduced.

First, the present inventors have studied (1) the case in which an abnormal value is included in the measured data.

Figure 7:
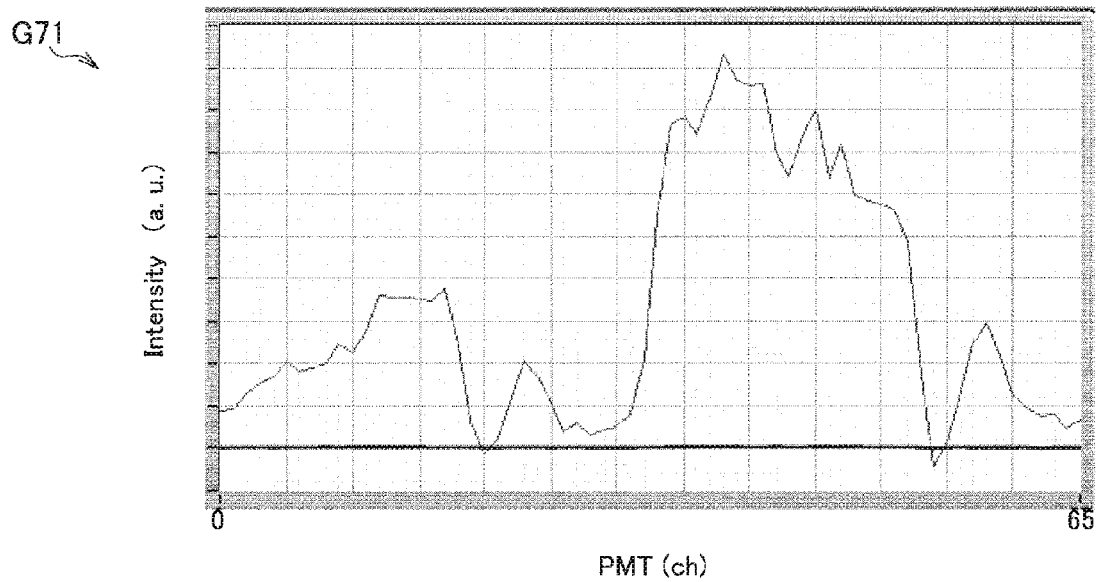
FIG. 7 is a diagram showing an example of a reference spectrum generated by the reference spectrum generation unit in the case where an abnormal value is included in measured data.
Figure 7:
Figure 7:
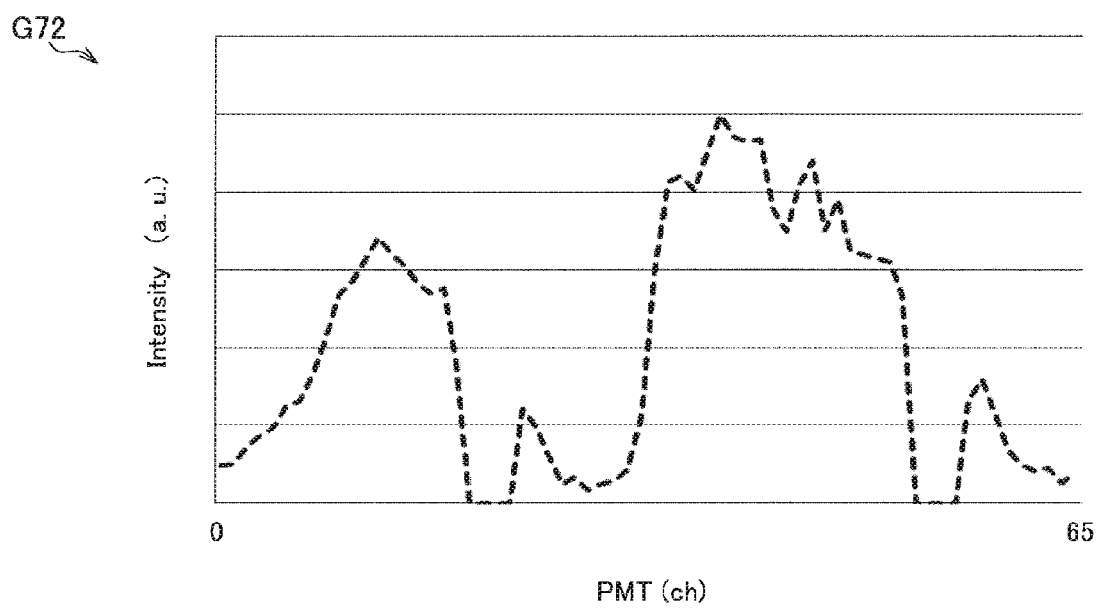

FIG. 7 is a diagram showing an example of a reference spectrum generated by the reference spectrum generation unit 103 in the case where an abnormal value is included in measured data. A graph G71 in FIG. 7 shows an example of a plurality of fluorescence spectra related to measured data used for generation of the reference spectrum, and a graph G72 in FIG. 7 shows an example of a reference spectrum generated on the basis of the plurality of fluorescence spectra shown in the graph G71. Note that a fluorochrome that labels microparticles used for generation of the reference spectrum shown in FIG. 7 is the fluorochrome A similarly to the case of FIG. 6.

A spectrum (referred to as an abnormal spectrum) mainly shown in the graph G71 is an imaginary spectrum obtained by multiplying a spectrum related to one piece of measured data by 100. That is, the abnormal spectrum indicates approximately 100 times the intensity of spectra related to other pieces of measured data. In the case of generating the reference spectrum using measured data related to such an abnormal spectrum, the peak resulting from autofluorescence particularly at 30 ch to 55 ch will be left even after subtraction of the averaged autofluorescence spectrum. Then, the peak resulting from autofluorescence may be left as it is in the reference spectrum, as shown in the graph G72. If the reference spectrum generated in this manner is used for analyzing the amount of fluorescence as the reference spectrum of the fluorochrome A, an incorrect analysis result may be obtained.

Figure 8:
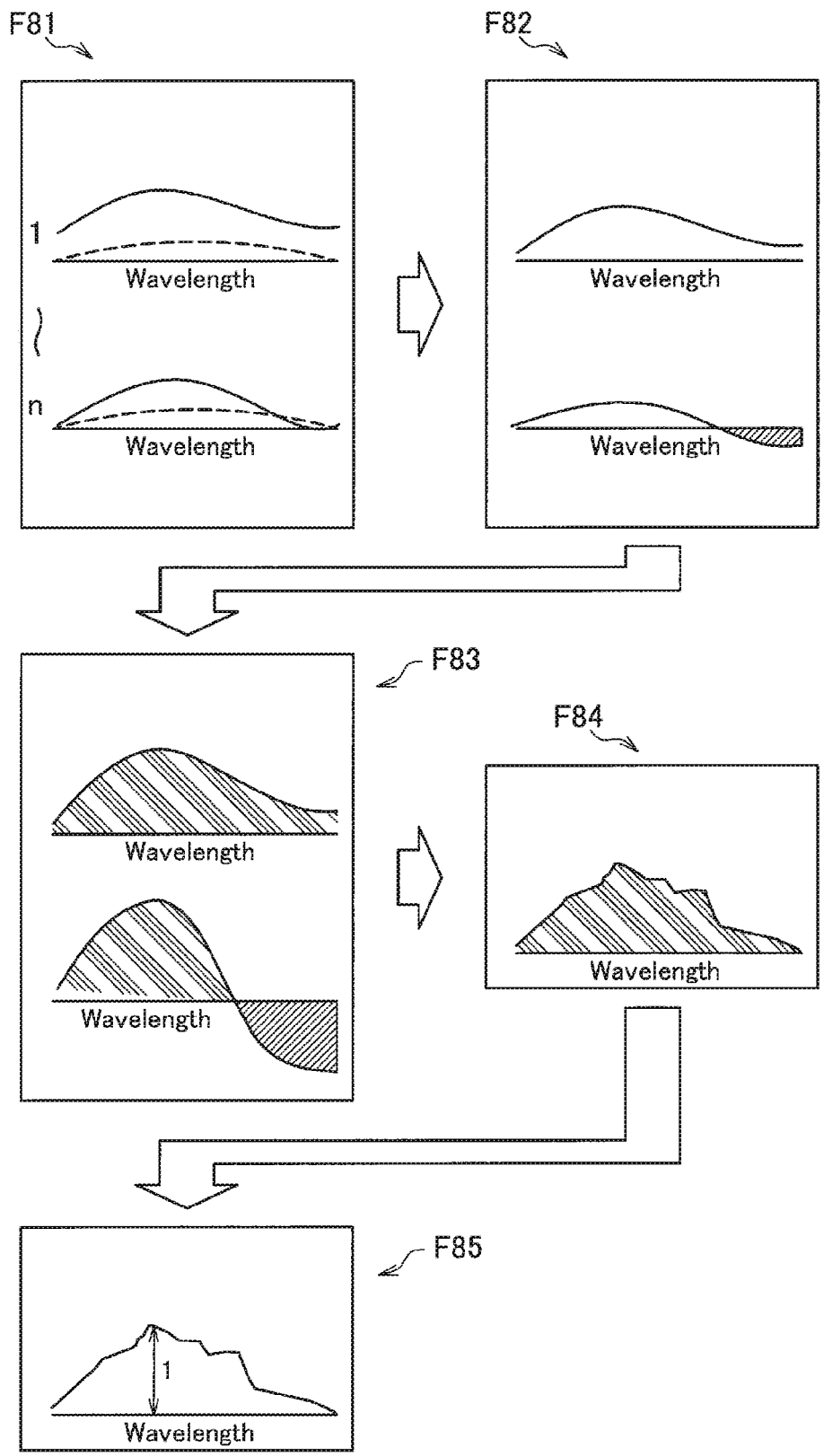
FIG. 8 is a diagram showing an example of a flow of reference spectrum generation processing.

In addition, the present inventors have studied (2) the case in which fluorescence is weak, and a noise included in a spectrum becomes relatively large. FIG. 8 is a diagram showing an example of a flow of reference spectrum generation processing. In FIG. 8, the case in which the intensity of a fluorescence spectrum n among a plurality of fluorescence spectra i (i=1 to n) is small is assumed.

First, as shown in a schematic spectrum F81 in FIG. 8, the averaged autofluorescence spectrum is subtracted from the plurality of fluorescence spectra i. On that occasion, for example, the intensities of some wavelength bands of the fluorescence spectrum n may become lower than the intensities of the wavelength bands of the averaged autofluorescence spectrum. This is because the signal intensities obtained in the wavelength bands of the fluorescence spectrum n are low, and are strongly affected by a negatively acting noise. In this case, as shown in a schematic spectrum F82 in FIG. 8, the intensities of some wavelength bands of the spectrum after subtraction indicate negative values.

Then, as shown in a schematic spectrum F83 in FIG. 8, in the processing of normalizing the total sum of the spectra after subtraction, the negative values are excessively weighted in the normalization. Accordingly, in the processing of averaging the spectra after normalization, a negatively affected averaged fluorescence spectrum is obtained as shown in a schematic spectrum F84 in FIG. 8, and thus, it is possible that the shape of the reference spectrum normalized by the spectrum intensity is significantly deviated from the shape of an actual fluorescence spectrum obtained from one fluorochrome, as shown in a schematic spectrum F85 in FIG. 8. In addition, it is possible in some cases that a negative intensity is included in the reference spectrum. In the case of using a reference spectrum including a negative intensity, in order to cancel the negative intensity in a wavelength band indicating the negative intensity in the analysis performed by the amount-of-fluorescence analysis unit 102, the amount of fluorescence of other fluorochromes that may indicate intensities in the wavelength band may be analyzed erroneously.

The event indicated in (1) in which an abnormal value is included in measured data may be caused by the state of a flow of microparticles in the microchannel, the size or mass of the microparticles, adhesion between the microparticles, or the like when generating measured data in the measurement device 20, for example. For example, light detected at a previous time may be detected again because of turbulence of the microparticles (carry-over). Accordingly, an abnormal value is included in the measured data. In addition, the event indicated in (2) in which fluorescence becomes weak may occur, for example, in the case where the amount of fluorescence that labels the microparticles is small, in the case where the intensity of light emitted from the fluorochrome or microparticles is low, or the like. The event indicted in (1) is an event that may occur accidentally in the measurement device 20. In addition, the event indicted in (2) is an event that may occur unavoidably depending on properties that microparticles as targets of measurement may inherently have or the amount of fluorescence of the fluorochrome used for analysis that may be included in the microparticles. Therefore, even if measured data including an abnormal spectrum or measured data including a weak spectrum is acquired when generating the reference spectrum, it is required to avoid using these pieces of measured data.

Therefore, the present inventors have arrived at the present technology in view of the above-described circumstances. That is, when generating the reference spectrum, an information processing device according to one embodiment of the present disclosure first extracts a spectrum indicating an outlier among a plurality of spectra (a group of spectra) obtained from microparticles that exhibit one fluorescent property through statistical processing, and excludes the extracted spectrum indicating an outlier from the above-described group of spectra. Then, the information processing device calculates the reference spectrum using the group of spectra from which the spectrum indicating an outlier has been excluded.

With such a configuration, an abnormal spectrum as described above can be excluded as an outlier through statistical processing. Hence, the accuracy of the reference spectrum can be improved.

In addition, when generating the reference spectrum of one fluorochrome, the information processing device according to one embodiment of the present disclosure performs the above-described statistical processing for each of a plurality of spectra (a first spectra group) obtained from microparticles labeled with one fluorochrome and a plurality of spectra (a second spectra group) obtained from microparticles not labeled with the one fluorochrome. Then, the information processing device excludes a spectrum indicating an outlier from each of the first spectra group and the second spectra group. Further, the information processing device averages each of the first spectra group and the second spectra group after exclusion of outliers, and subtracts the average spectrum of the second spectra group from the average spectrum of the first spectra group to calculate the reference spectrum.

With such a configuration, since noises are smoothed by averaging upon excluding outliers, a negative intensity can be made less likely to be included in the reference spectrum of noises. Hence, even if a signal related to fluorescence or autofluorescence obtained from microparticles is weak, the accuracy of the reference spectrum can be improved.

Hereinafter, detailed functions and processing of the reference spectrum generation unit 103 included in the information processing device 10 according to a first embodiment and a second embodiment will be described.

2. First Embodiment (Generation of Reference Spectrum Corresponding to Fluorochrome)

2.1. Configuration of Reference Spectrum Generation Unit

Figures 9, 10:
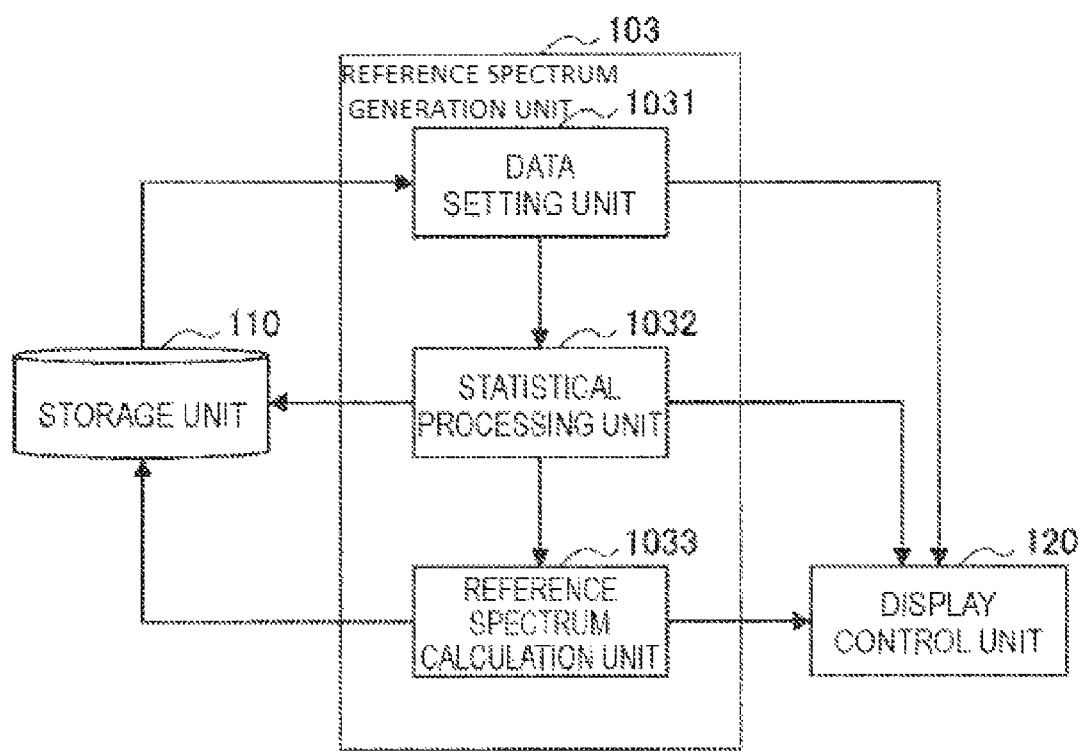
FIG. 9 is a functional block diagram showing an example of a functional configuration of a reference spectrum generation unit according to a first embodiment of the present disclosure.
FIG. 10 is a diagram for describing fluorochrome selection processing performed by a data setting unit according to the embodiment.

FIG. 9 is a functional block diagram showing an example of a functional configuration of the reference spectrum generation unit 103 according to the first embodiment of the present disclosure. As shown in FIG. 9, the reference spectrum generation unit 103 according to the present embodiment includes a data setting unit 1031, a statistical processing unit 1032, and a reference spectrum calculation unit 1033.

(Data Setting Unit)

The data setting unit 1031 according to the present embodiment acquires measured data to be used for generation of the reference spectrum from the storage unit 110, and performs setting and the like of data to be used for subsequent processing. For example, the data setting unit 1031 may perform (a) selection of a light-emitting element, (b) acquisition of measured data, and (c) correction of measured data.

Selection of Light-Emitting Element

First, the data setting unit 1031 according to the present embodiment selects a light-emitting element related to the reference spectrum which is a target of generation. Note that the light-emitting element in the present specification includes one substance, microparticle, and the like that exhibits one response property with respect to light. For example, the substance means a fluorochrome, for example.

For example, the data setting unit 1031 selects a light-emitting element related to the reference spectrum which is a target of generation through user's selection. FIG. 10 is a diagram for describing fluorochrome selection processing performed by the data setting unit 1031 according to the present embodiment. In the first column of the table shown in FIG. 10, identification symbols (CD1, CD2, . . . , Neg) of light-emitting elements are indicated, and types (FITC, PE, . . . , Negative) of the light-emitting elements such as fluorochromes corresponding to the respective identification symbols are indicated in the second column. Here, Neg (Negative) in the table means an unstained microparticle (autofluorescence). The fluorochromes shown in the table of FIG. 10 may be fluorochromes corresponding to measured data stored in the storage unit 110, or may be all or part of fluorochromes whose spectra can be measured by the measurement device 20.

Note that, when performing processing of generating the reference spectrum of a fluorochrome, not only measured data corresponding to a fluorochrome which is a target of generation of the reference spectrum, but also measured data corresponding to unstained microparticles is selected.

In addition, the display control unit 120 may cause a display device or the like to display the table shown in FIG. 10. In this case, the data setting unit 1031 may select a light-emitting element related to the reference spectrum which is a target of generation through an operation performed by a user having viewed the table. Specifically, the data setting unit 1031 may select a light-emitting element related to the reference spectrum which is a target of generation among the light-emitting elements shown in the table through a user operation.

Note that, in the case where a fluorochrome related to the reference spectrum which is a target of generation does not exist in the table shown in FIG. 10 in the light-emitting element selection processing, for example, the data setting unit 1031 may perform processing of adding the fluorochrome to the table through an input operation or the like by the user.

Acquisition of Measured Data

Next, the data setting unit 1031 according to the present embodiment acquires measured data corresponding to the selected light-emitting element from the storage unit 110. The acquired measured data may be, for example, measured data acquired by the measurement device 20 for fluorescence emitted from microparticles labeled with the selected fluorochrome, or measured data acquired by the measurement device 20 for autofluorescence of microparticles. The measured data includes spectra obtained from the microparticles. The spectra include, for example, fluorescence spectra or autofluorescence spectra related to fluorescence or autofluorescence emitted from the microparticles. Measurement of fluorescence or autofluorescence may be previously performed prior to the reference spectrum generation processing, or may be performed in parallel to the reference spectrum generation processing.

Note that, in the case of generating the reference spectrum of one fluorochrome, it is preferable that the measurement device 20 acquires measured data of microparticles labeled only with the one fluorochrome. In addition, in order to suppress an influence upon the fluorescence spectra obtained by autofluorescence derived from microparticles, it is preferable that microparticles to be used for generation of the reference spectrum are unified by the same type of particles that may exhibit the same autofluorescence spectrum.

Figure 11:
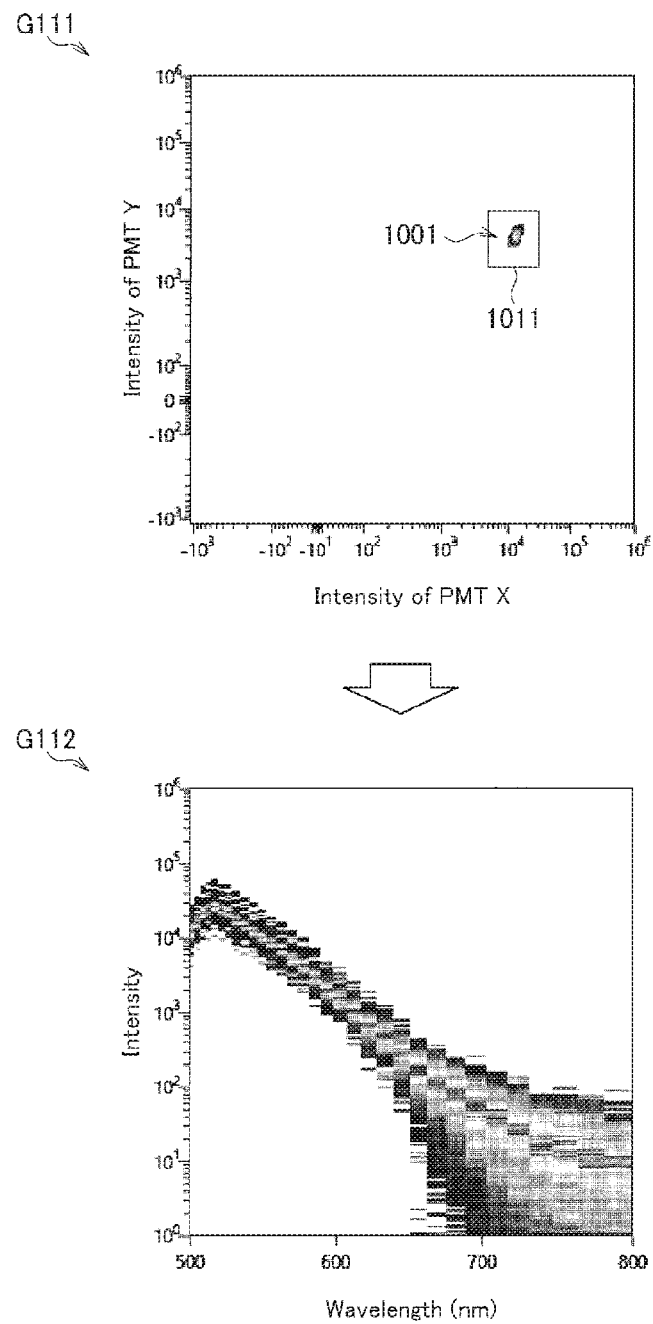
FIG. 11 includes a diagram for describing measured data acquisition processing in the case where FITC is selected and a diagram showing an example of the distribution of fluorescence spectra related to acquired measured data.
Figure 12:
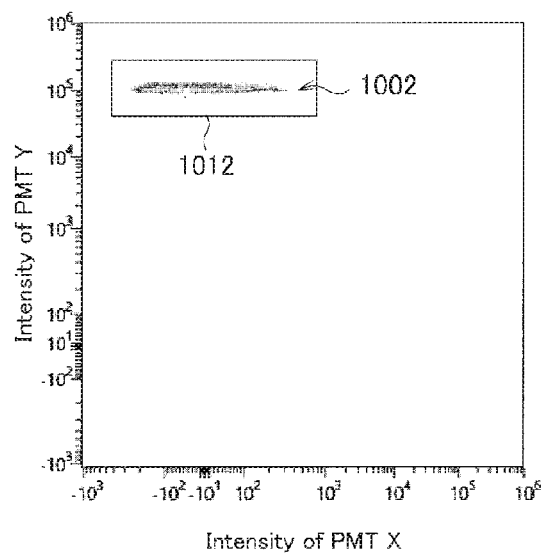
FIG. 12 includes a diagram for describing measured data acquisition processing in the case where PE is selected and a diagram showing an example of the distribution of fluorescence spectra related to acquired measured data.
Figure 12:
Figure 12:
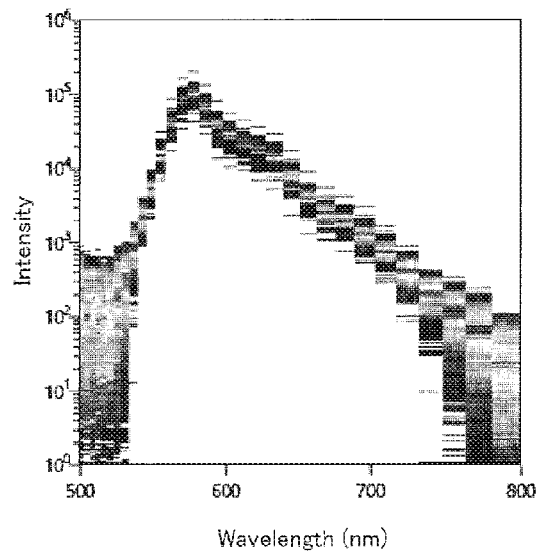
Figure 13:
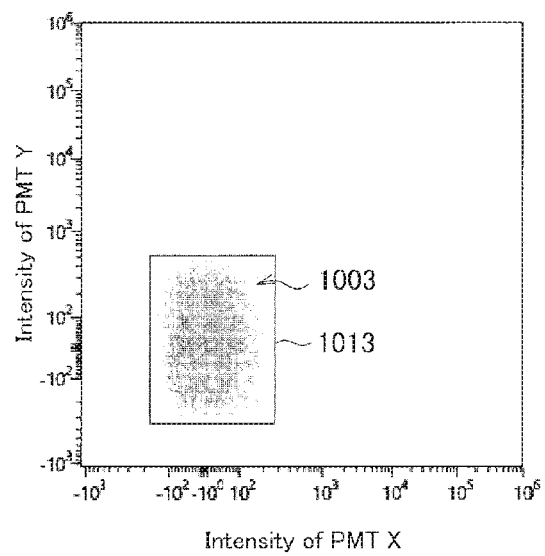
FIG. 13 includes a diagram for describing measured data acquisition processing in the case where Negative (unstained) is selected and a diagram showing an example of the distribution of fluorescence spectra related to acquired measured data.
Figure 13:
Figure 13:
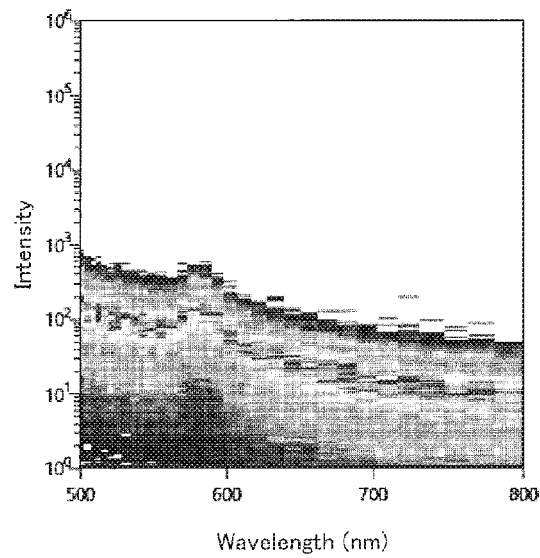

For example, the data setting unit 1031 acquires measured data corresponding to the selected light-emitting element from the storage unit 110 through user's selection. FIG. 11 to FIG. 13 are diagrams for describing measured data acquisition processing in the case where FITC, PE, and Negative (unstained) are selected, and are diagrams showing examples of the distribution of fluorescence spectra related to the acquired measured data. A graph G111 and a graph G112 in FIG. 11 are a diagram showing the distribution of fluorescence intensities in specific wavelengths of the fluorescence spectrum of FITC and a diagram showing integrated data of the fluorescence spectrum of FITC. A graph G121 and a graph G122 in FIG. 12 are a diagram showing the distribution of fluorescence intensities in specific wavelengths of the fluorescence spectrum of PE and a diagram showing integrated data of the fluorescence spectrum of PE. A graph G131 and a graph G132 in FIG. 13 are a diagram showing the distribution of fluorescence intensities in specific wavelengths of the fluorescence spectrum of Negative and a diagram showing integrated data of the fluorescence spectrum of Negative. Note that the horizontal axis and the vertical axis in the graph G111, the graph G121, and the graph G131 in FIG. 11 to FIG. 13 indicate fluorescence intensities detected in an X channel and a Y channel of PMT (that is, fluorescence intensities in first and second wavelength bands corresponding to the X channel and the Y channel). In addition, the horizontal axis in the graph G112, the graph G122, and the graph G132 in FIG. 11 to FIG. 13 indicates the wavelength. The fluorescence spectrum obtained for each microparticle is a spectrum including fluorescence intensities detected in a plurality of PMTs. In addition, contour colors shown in the graph G112, the graph G122, and the graph G132 correspond to integrated data of a plurality of fluorescence spectra related to measured data.

Referring to FIG. 11, the data setting unit 1031 first acquires measured data about microparticles labeled with FITC from the storage unit 110. Then, the data setting unit 1031 may cause an intensity distribution chart as shown in the graph G111 to be displayed on a display device or the like by the display control unit 120. For example, as shown in the graph G111, fluorescence intensities in the first wavelength band and the second wavelength band of the fluorescence spectrum related to the acquired measured data may be plotted. A plot 1001 corresponds to measured data related to a group of microparticles labeled with FITC.

Next, the data setting unit 1031 selects the plot 1001 by a user operation or the like. For example, as shown in the graph G111, the data setting unit 1031 may set a frame 1011 so as to enclose the plot 1001 through an input operation or the like by the user. Accordingly, measured data corresponding to the plot enclosed by the frame 1011 is acquired. The shape and size of the frame 1011, and the method of setting the frame 1011 are not particularly limited.

The graph G112 indicates integrated data of fluorescence spectra related to the measured data shown in the graph G111. The integrated data may be displayed on the display device or the like by the display control unit 120. Accordingly, the user can check the validity of the acquired measured data.

Also for measured data related to PE and Negative related to FIG. 12 and FIG. 13, measured data corresponding to a plot 1002 enclosed by a frame 1012 and a plot 1003 enclosed by a frame 1013 are acquired by the data setting unit 1031, similarly to the example shown in FIG. 11. Note that the data setting unit 1031 may acquire all pieces of measured data related to the fluorochrome selected in the light-emitting element selection processing from the storage unit 110. That is, the data setting unit 1031 may acquire all pieces of measured data related to the fluorochrome at the time point when a light-emitting element is selected, without performing measured data selection and acquisition processing as shown in FIG. 11 to FIG. 13.

Correction of Measured Data

Further, the data setting unit 1031 may perform processing of correcting the acquired measured data. Correction as stated herein is, for example, correction for non-uniformity of photoelectric conversion properties in PMTs or variations in flowing position of microparticles within the microchannel. These corrections may be performed on the basis of a technology described in JP2013-61244A or WO2013/183345, for example.

Note that the correction processing may be performed previously by the measurement device 20, or may be performed by the measured data acquisition unit 101 or the like shown in FIG. 4. In this case, since measured data after correction is stored in the storage unit 110, the data setting unit 1031 may not perform correction processing again. In addition, the correction processing may not necessarily be performed.

In addition, the function related to the correction processing may not necessarily be included in the reference spectrum generation unit 103. For example, the function related to the correction processing may be executed by the measured data acquisition unit 101, or may be executed as a function that the information processing device 10 has. In addition, the correction processing may also be performed in the above-described amount-of-fluorescence analysis unit 102.

The data setting unit 1031 sets measured data concerning a light-emitting element related to the reference spectrum which is a target of generation by performing the above processing. The set measured data is output to the statistical processing unit 1032. In addition, the set measured data may be stored in the storage unit 110.

(Statistical Processing Unit)

The statistical processing unit 1032 according to the present embodiment performs statistical processing for a group of spectra obtained by applying light to a group of microparticles that exhibit one response property with respect to light, and on the basis of the result of the statistical processing, excludes a spectrum indicating an outlier from the group of spectra. Specifically, the statistical processing unit 1032 performs statistical processing for a plurality of spectra (a group of spectra) related to measured data, and on the basis of the result of the statistical processing, excludes a spectrum indicating an outlier from the group of spectra. Here, one response property with respect to light indicates a fluorescent property, for example. The fluorescent property means a property related to fluorescence derived from a fluorochrome that labels microparticles, or a property related to autofluorescence derived from unstained microparticles. In addition, a group of microparticles that exhibit one response property with respect to light means that each of the group of microparticles exhibits a similar response property. For example, one response property with respect to light exhibited by the group of microparticles may be a similar fluorescent property obtained from simply-stained or multi-stained microparticles, or may be a fluorescent property related to autofluorescence obtained from unstained microparticles. The group of spectra corresponding to these response properties may have spectra of a similar shape as a whole although some shifts exist among microparticles.

Here, the outlier is an outlier for the intensities of a plurality of spectra. For example, in the case where the intensity in any wavelength band of one spectrum among a plurality of spectra is significantly deviated from the intensities in the wavelength band of the others of the plurality of spectra, the one spectrum may be a spectrum indicating an outlier. In addition, in the case where the shape of one spectrum among a plurality of spectra is significantly deviated from the shapes of the others of the plurality of spectra, the one spectrum may be a spectrum indicating an outlier. The degree (threshold value) of deviation in the intensity or shape of the above-described spectrum is determined in accordance with the above-described statistical processing.

The statistical processing unit 1032 according to the present embodiment performs reference spectrum setting processing through use of RANdom SAmple Consensus (RANSAC) as an example of statistical processing for excluding a spectrum indicating an outlier. Hereinafter, the setting processing will be described with reference to FIG. 14 and FIG. 15.

Setting of Reference Spectrum Through Use of RANSAC

Figure 14:
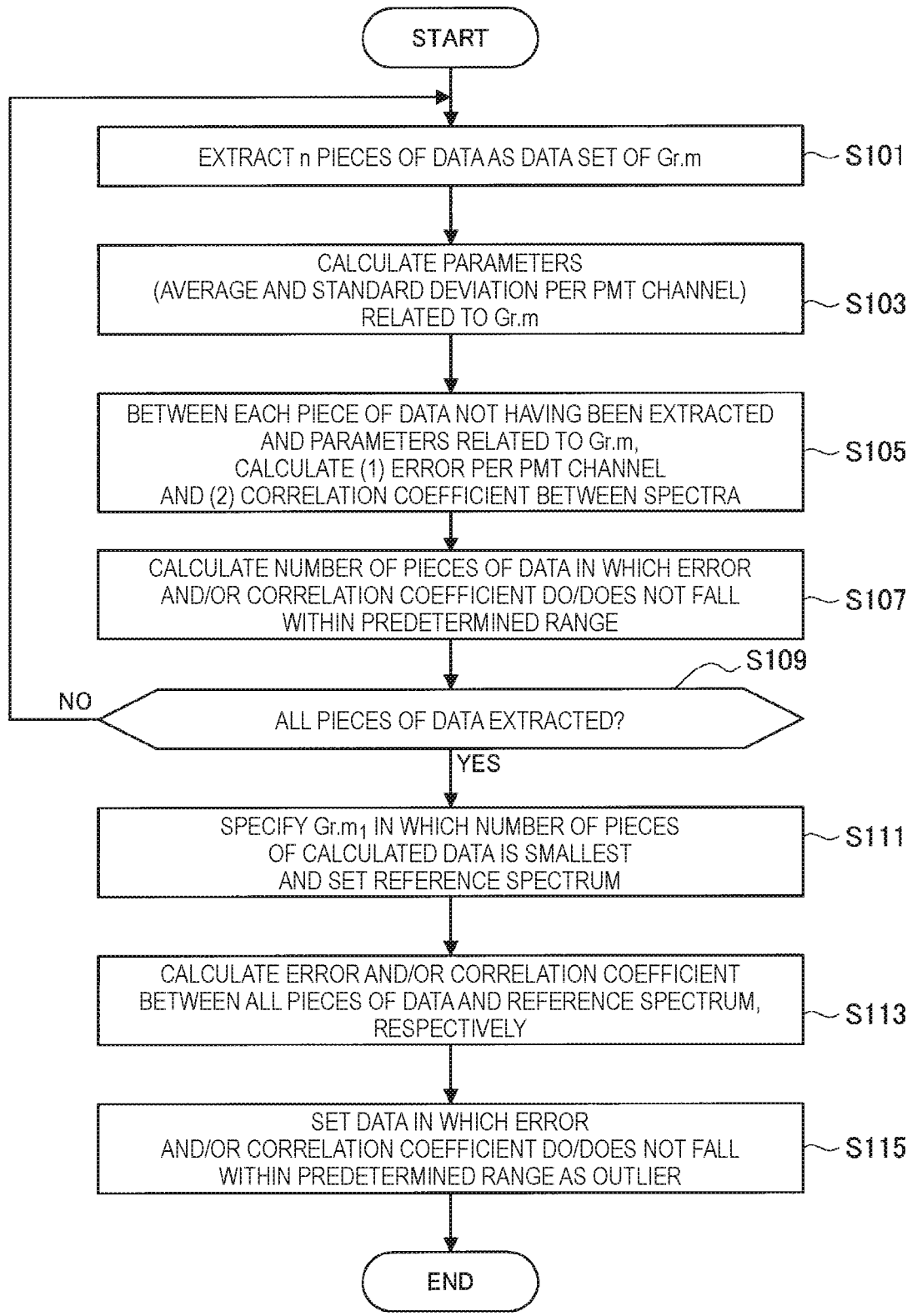
FIG. 14 is a flow chart related to an example of reference spectrum setting processing performed by a statistical processing unit according to the embodiment through use of RANSAC.
Figure 15:
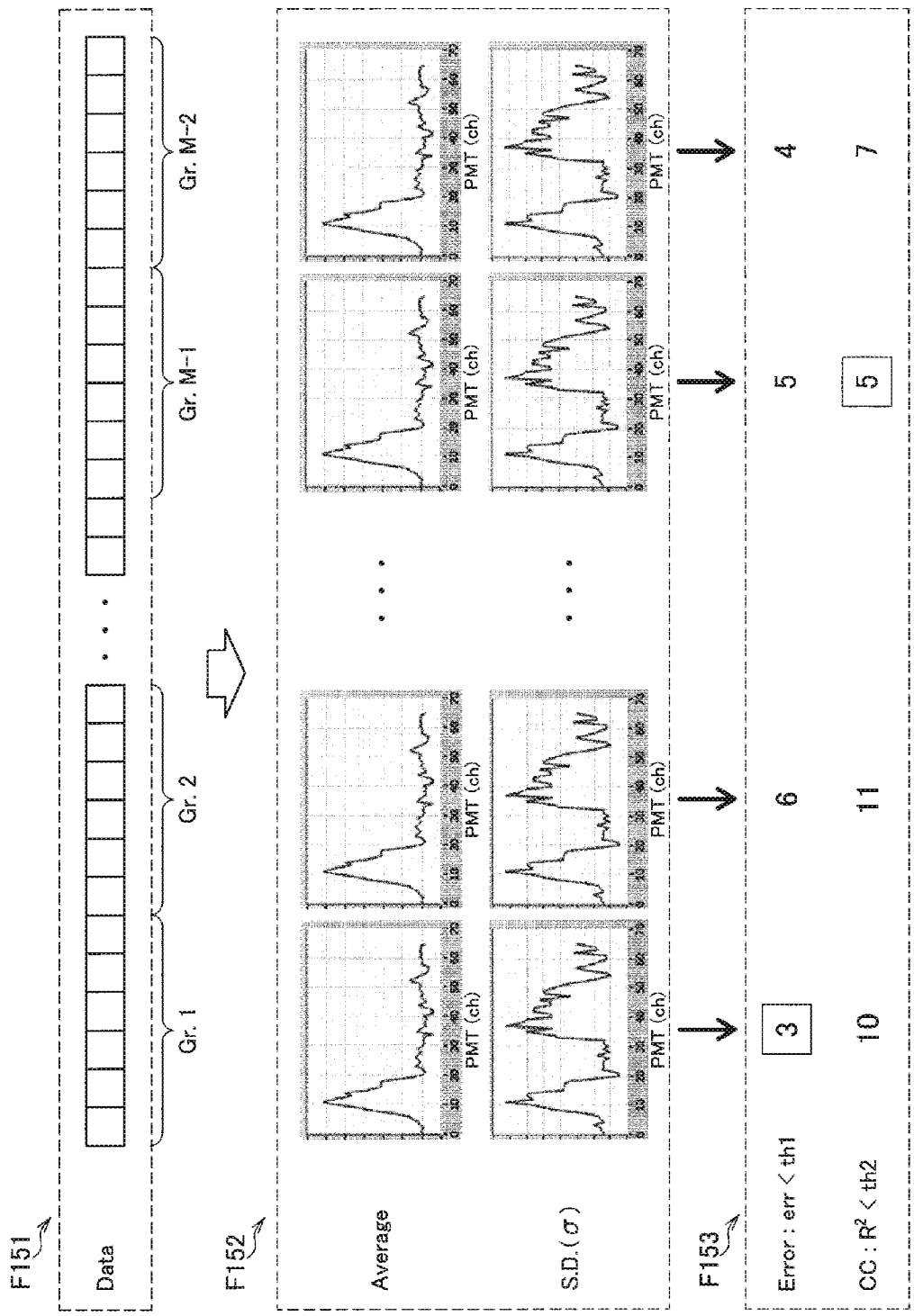
FIG. 15 is a diagram for describing an example of reference spectrum setting processing performed by the statistical processing unit according to the embodiment.

FIG. 14 is a flow chart related to an example of reference spectrum setting processing through use of RANSAC performed by the statistical processing unit 1032 according to the present embodiment. In addition, FIG. 15 is a diagram for describing an example of reference spectrum setting processing performed by the statistical processing unit 1032 according to the present embodiment. Note that, as a precondition in the setting processing, it is assumed that N pieces of measured data related to one fluorochrome (assumed as the fluorochrome A) have been set by the data setting unit 1031. Here, the number N of pieces of measured data to be used for the setting processing is not particularly limited, but is preferably more than or equal to a predetermined number in order to exclude a spectrum indicating an outlier. The predetermined number may be, for example, twice the number n of pieces of data to be extracted in step S101 below.

Referring to FIG. 14, the statistical processing unit 1032 first extracts n pieces of measured data from the N pieces of measured data as a data set of Gr.m (m=1 to M) (S101). Specifically, referring to a schematic view F151 in FIG. 15, the statistical processing unit 1032 sets M data sets including Gr.1, Gr.2, . . . , and Gr.M for the N pieces of measured data. For each of these data sets having been set, the statistical processing unit 1032 performs processing which will be described later. Note that the number n of pieces of measured data included in one data set is not particularly limited.

Next, the statistical processing unit 1032 calculates parameters related to Gr.m from measured data included in the data set of Gr.m (S103). Here, the parameters related to Gr.m refer to an average value and a standard deviation of spectra of measured data included in the data set of Gr.m. More specifically, the statistical processing unit 1032 calculates an average value and a standard deviation per PMT channel of measured data included in the data set of Gr.m. For example, assume that measured data included in the data set of Gr.m is D (m, k) (k=1 to n), and the intensity of a PMT channel 1 (l=1 to L: L is the number of PMT channels) included in D (m, k) is I (m, k, l). In this case, the statistical processing unit 1032 calculates an average value $ave_I$ (m, l) and a standard deviation $\sigma_I$ (m, l) of the intensity of the PMT channel 1 for each PMT channel. The average value $ave_I$ (m, l) and the standard deviation $\sigma_I$ (m, l) become parameters related to Gr.m.

Next, the statistical processing unit 1032 compares measured data other than the data set of Gr.m and parameters related to Gr.m (S105). Specifically, the statistical processing unit 1032 may calculate an error err (m, p, k, l) between the intensity I (p, k, l) of the PMT channel 1 included in each piece of measured data D (p, k) (p≠m) and the average value $ave_I$ (m, l), respectively. In addition, the statistical processing unit 1032 may calculate a correlation coefficient $R^2$ (m, p, k) between a spectrum $S_D$ (p,k) expressed by the intensity I (p, k, l) of the measured data D (p, k) and a spectrum $S_{ave}$ (m) expressed by the average value $ave_I$ (m, l), respectively. The spectrum $S_D$ (p, k) is a spectrum including the intensity I in all the PMT channels, and the spectrum $S_{ave}$ (m) is a spectrum including the average value $ave_I$ (m, l) related to all the PMT channels.

Next, the statistical processing unit 1032 verifies whether or not the error and correlation coefficient obtained in step S105 are included in predetermined ranges for each piece of measured data except the data set of Gr.m, and calculates the number of pieces of measured data (outlier-containing measured data) in which the error and the correlation coefficient are not included in the predetermined ranges (S107). Specifically, in the case of calculating the number of pieces of outlier-containing measured data on the basis of the error, the statistical processing unit 1032 may first verify whether or not the error err (m, p, k, l) falls below a first predetermined threshold value th1 per PMT channel of each piece of measured data. At this time, for example, if one of l errors err (m, p, k, l) included in the measured data (p, k) falls below the above-described first predetermined threshold value th1, the statistical processing unit 1032 may count the measured data as outlier-containing measured data. Note that the first predetermined threshold value th1 may be set on the basis of the standard deviation $\sigma_I$ (m, l) related to the data set of Gr.m.

In addition, in the case of calculating the number of pieces of outlier-containing measured data on the basis of the correlation coefficient, the statistical processing unit 1032 may verify whether or not the correlation coefficient $R^2$ (m, p, k) falls below a second predetermined threshold value th2 for each piece of measured data. Note that the second predetermined threshold value th2 may be set as appropriate on the basis of the number of pieces of calculated outlier-containing measured data, the accuracy of a reference spectrum to be obtained subsequently, or the like.

The statistical processing unit 1032 performs processing related to step S105 and step S107 for all pieces of measured data except the data set of Gr.m (S109). The statistical processing unit 1032 calculates at least either of the number $N_{err}$ (m) of pieces of outlier-containing measured data related to the error about the data set of Gr.m and the number $N_{cor}$ (m) of pieces of outlier-containing measured data related to the correlation coefficient, from the above-described processing result.

The statistical processing unit 1032 repeatedly performs processing related to the above-described steps S101 to S107 for all the data sets (Gr.1 to Gr.M). Accordingly, as shown in a schematic view F152 and a table F153 in FIG. 15, parameters (the average value $ave_I$ (m, l) and the standard deviation $\sigma_I$ (m, l)) are calculated for all the data sets, and in addition, at least either of the number $N_{err}$ (m) of pieces of outlier-containing measured data related to the error and the number $N_{cor}$ (m) of pieces of outlier-containing measured data related to the correlation coefficient is calculated for all the data sets.

When parameters are calculated and the number of pieces of outlier-containing measured data is calculated for all the data sets (YES in S109 of FIG. 14), the statistical processing unit 1032 specifies a data set $Gr.m_1$ in which the number of pieces of outlier-containing measured data is the smallest (S111). Specifically, as shown in the table F153, the statistical processing unit 1032 specifies, as $Gr.m_1$, a data set in which at least either of the number $N_{err}$ (m) of pieces of outlier-containing measured data related to the error (Error) and the number $N_{cor}$ (m) of pieces of outlier-containing measured data related to the correlation coefficient (CC) is the smallest. In the example shown in the table F153, a data set in which the number $N_{err}$ (m) of pieces of outlier-containing measured data related to the error is the smallest is Gr.1. In addition, a data set in which the number $N_{cor}$ (m) of pieces of outlier-containing measured data related to the correlation coefficient is the smallest is Gr.M−1.

Measured data included in the data set of $Gr.m_1$ specified here is a measured data group having the fewest variations. Thus, the data set becomes the most appropriate data set for setting the reference spectrum to be used as a reference for specifying a spectrum indicating an outlier. Note that, for specification of $Gr.m_1$, whether to use either the number $N_{err}$ (m) of pieces of outlier-containing measured data related to the error or the number $N_{cor}$ (m) of pieces of outlier-containing measured data related to the correlation coefficient will be described later.

In addition, the statistical processing unit 1032 sets the reference spectrum on the basis of the data set of $Gr.m_1$. For example, the statistical processing unit 1032 may set a spectrum indicated by the average value $ave_I$ ($m_1$, l) which is a parameter related to the data set of $Gr.m_1$ as the reference spectrum.

Next, the statistical processing unit 1032 calculates an error and a correlation coefficient between spectra related to all pieces of measured data and the reference spectrum, respectively (S113 in FIG. 14). Specifically, in the case of calculating the error, the statistical processing unit 1032 may calculate an error err ($m_1$, m, k, l) between the intensity I (m, k, l) included in the measured data (m, k) and the average value $ave_I$ ($m_1$, l) per PMT channel of all pieces of measured data, respectively. In addition, in the case of calculating the correlation coefficient, the statistical processing unit 1032 may calculate the correlation coefficient $R^2$ ($m_1$, m, k) between a spectrum $S_D$ (m, k) expressed by the intensity I (m, k, l) and the spectrum $S_{ave}$ ($m_1$) expressed by the average value $ave_I$ ($m_1$, l) for all pieces of measured data, respectively. These types of calculation processing may be similar to the processing related to step S105.

Next, the statistical processing unit 1032 verifies whether or not the error and correlation coefficient obtained in step S113 are included in predetermined ranges for each of all pieces of measured data, and sets measured data in which the error and the correlation coefficient are not included in the predetermined ranges as measured data (outlier-containing measured data) including a spectrum indicating an outlier (S115).

Specifically, in the case of specifying outlier-containing measured data on the basis of the error, the statistical processing unit 1032 may first verify whether or not the error err ($m_1$, m, k, l) falls below a third predetermined threshold value th3 per PMT channel of each piece of measured data. At this time, for example, if even one of the l errors err ($m_1$, m, k, l) included in the measured data (m, k) falls below outside the above-described third predetermined threshold value th3, the statistical processing unit 1032 may specify that the measured data is outlier-containing measured data. Note that the third predetermined threshold value th3 may be set on the basis of the standard deviation $\sigma_I$ ($m_1$, l) related to the data set of $Gr.m_1$. In addition, the third predetermined threshold value th3 may be identical to the above-described first predetermined threshold value th1.

In addition, in the case of specifying outlier-containing measured data on the basis of the correlation coefficient, the statistical processing unit 1032 may verify whether or not the correlation coefficient $R^2$ ($m_1$, m, k) falls below a fourth predetermined threshold value th4 for each piece of measured data. Note that the fourth predetermined threshold value th4 may be set as appropriate on the basis of the number of pieces of calculated outlier-containing measured data, the accuracy of the reference spectrum to be obtained subsequently, or the like. In addition, the fourth predetermined threshold value th4 may be identical to the above-described second predetermined threshold value th2.

The statistical processing unit 1032 can specify measured data including an outlier in accordance with a flow chart shown in FIG. 14. The statistical processing unit 1032 excludes the specified measured data from a group of measured data corresponding to a group of spectra. That is, the statistical processing unit 1032 excludes a spectrum indicating an outlier from a group of spectra. The group of measured data after measured data including an outlier is excluded is output to the reference spectrum calculation unit 1033 which will be described later. Note that the situation of processing performed by the statistical processing unit 1032 and the result of processing may be stored in the storage unit 110 as appropriate, or may be displayed on a display device or the like as appropriate by the display control unit 120.

Difference in Excluding Condition

As described above, the statistical processing unit 1032 specifies outlier-containing measured data on the basis of an excluding condition of at least either the error or correlation coefficient. The tendencies of shapes of spectra related to outlier-containing measured data specified for respective excluding conditions are different from each other.

Figure 16:
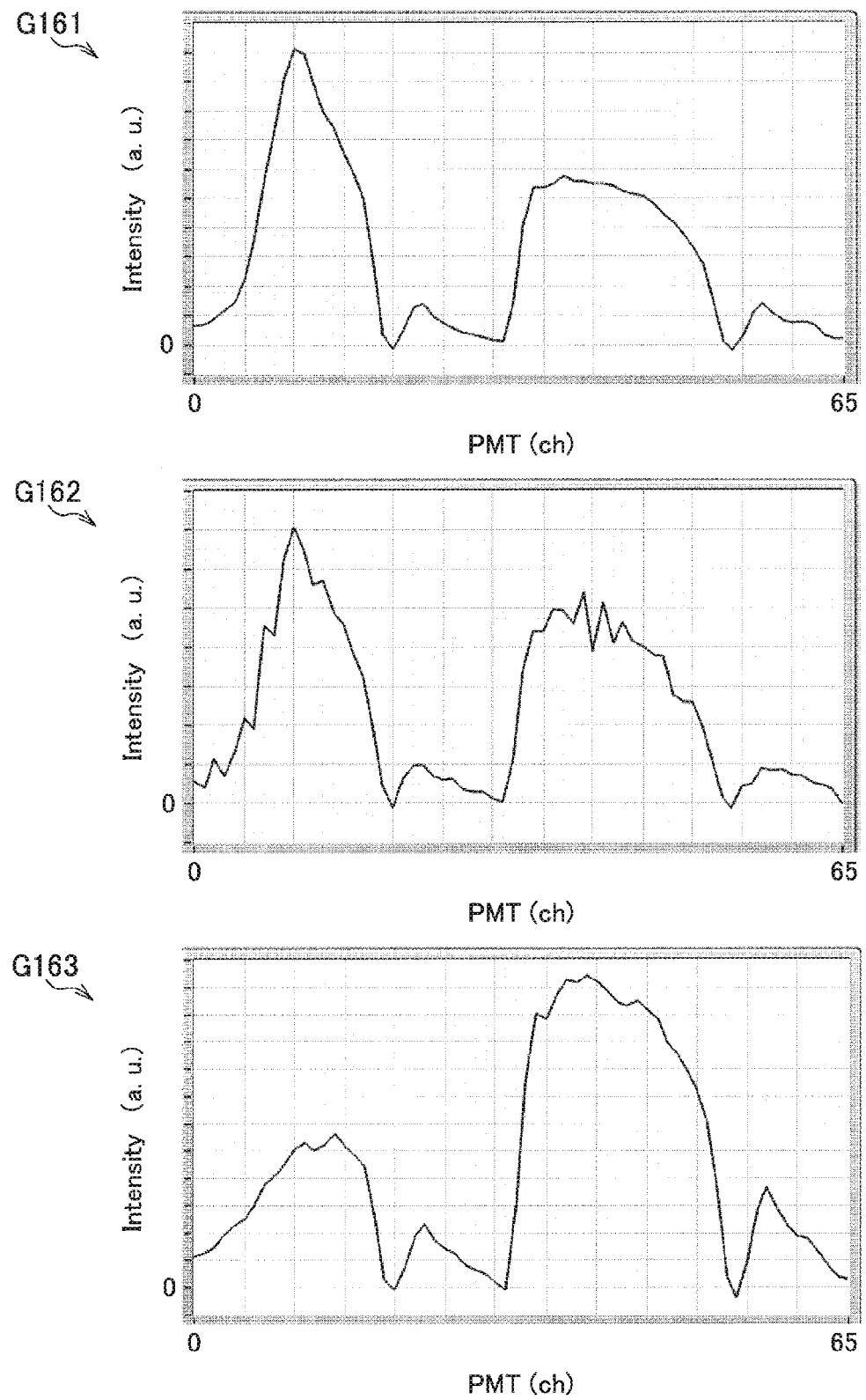
FIG. 16 includes diagrams showing an average spectrum of spectra related to measured data including or not including outliers.

FIG. 16 is a diagram showing average spectra of spectra related to measured data including or not including an outlier. A graph G161 in FIG. 16 is an average spectrum (effective average spectrum) of spectra related to measured data not including an outlier. A graph G162 in FIG. 16 is an average spectrum (error-induced outlier-containing average spectrum) of spectra related to outlier-containing measured data specified on the basis of the error. In addition, a graph G163 in FIG. 16 is an average spectrum (correlation coefficient-induced outlier-containing average spectrum) of spectra related to outlier-containing measured data specified on the basis of the correlation coefficient.

First, when comparing the spectra shown in the graph G161 and the graph G162, it is shown that many noise components are included in the error-induced outlier-containing average spectrum. This may result from detection of an abnormal value or a strong noise in at least any of the PMTs that output intensities included in the spectra.

In addition, when comparing the spectra shown in the graph G161 and the graph G163, it is shown that the shapes of two peaks exhibited by the correlation coefficient-induced outlier-containing average spectrum are significantly deviated from the shapes of two peaks exhibited by the effective average spectrum. That is, the shape of the correlation coefficient-induced outlier-containing average spectrum and the shape of the effective average spectrum are significantly different. This may result from the type of microparticles or the labeling state of fluorochromes measured by the measurement device 20.

In this manner, a spectrum including an abnormal value or a strong noise is excluded under an excluding condition related to the error, while a spectrum whose shape of the spectrum is different from the shapes of a large number of other spectra is excluded under an excluding condition related to the correlation coefficient. Such excluding conditions may be changed in accordance with the type of spectra obtained from microparticles, used in calculation of the reference spectrum.

Although detailed description will be provided for the reference spectrum calculation unit 1033, in the case of generating the reference spectrum of the fluorochrome A, for example, fluorescence spectra (the first spectra group) obtained from microparticles labeled only with the fluorochrome A and fluorescence spectra (the second spectra group) of unstained microparticles are used. The statistical processing unit 1032 excludes a spectrum indicating an outlier from each of the first spectra group and the second spectra group prior to calculation of the reference spectrum of the fluorochrome A.

The statistical processing unit 1032 may use the excluding condition related to the correlation coefficient as an excluding condition for excluding a spectrum indicating an outlier from the first spectra group. As described above, for analyzing the amount of fluorescence by deconvolution of fluorescence spectra derived from a plurality of fluorochromes, high accuracy of the shape of the generated reference spectrum is required. Thus, by excluding a spectrum indicating an outlier on the basis of the correlation coefficient related to the spectrum shape, only spectra having similar shapes can be obtained as the first spectra group. Therefore, the accuracy of the reference spectrum to be calculated in subsequent processing can be increased.

In addition, the statistical processing unit 1032 may use the excluding condition related to the error as an excluding condition for excluding a spectrum indicating an outlier from the second spectra group. Since spectra included in the second spectra group are autofluorescence spectra, it is highly likely that the spectra are not necessarily uniform in shape in accordance with the shape, size, property, or the like of microparticles. Thus, in the case of using the excluding condition related to the correlation coefficient, the number of spectra specified as spectra indicating outliers will be increased. Then, the accuracy of the reference spectrum to be calculated in subsequent processing can be reduced since the denominator of spectra is reduced. Therefore, in the case of excluding a spectrum indicating an outlier from the second spectra group, the spectrum indicating an outlier may be excluded only using the excluding condition related to the error.

In this manner, in the processing related to exclusion of a spectrum indicating an outlier, excluding conditions different between the first spectra group and the second spectra group may be used. That is, appropriate excluding conditions may be used in accordance with the shape uniformity of spectra included in each of the spectra group, or the like. Accordingly, the accuracy of the generated reference spectrum can be improved.

Note that the statistical processing unit 1032 may further use the excluding condition related to the error as an excluding condition for excluding a spectrum indicating an outlier from the first spectra group. Accordingly, a spectrum having high correlation of spectrum shape but including an abnormal value or the like can be excluded from the first spectra group.

Evaluation of Uniformity

In addition, the statistical processing unit 1032 may evaluate the uniformity of a group of spectra (measured data) used for generation of the reference spectrum, using the result of statistical processing for specifying and excluding a spectrum indicating an outlier from the group of spectra.

Here, the result of statistical processing may be, for example, the number of pieces of measured data in which the error or correlation coefficient falls outside the predetermined range, calculated in step S107 of FIG. 14. If this number of pieces of outlier-containing measured data is large as a whole, it is understood that measured data used for generation of the reference spectrum is not high. In addition, if the number of pieces of outlier-containing measured data calculated using an average value or the like related to some data sets is large, it is understood that the uniformity of measured data included in the some data sets is not high.

In addition, the result of statistical processing may be the correlation coefficient calculated in step S113 of FIG. 14, for example. It is understood that, if the correlation coefficient is high, the uniformity of measured data is high, and if the correlation coefficient is low, the uniformity of measured data is not high.

Information related to such an evaluation of the uniformity of measured data may be displayed on the display device by the display control unit 120. Accordingly, the user can learn the uniformity of measured data used for generation of the reference spectrum.

An example of processing performed by the statistical processing unit 1032 has been described so far. Note that the statistical processing unit 1032 according to the present embodiment performs processing of excluding measured data including an outlier (a spectrum indicating an outlier) through statistical processing by means of robust estimation such as RANSAC, whilst the present technology is not limited to such an example. For example, the statistical processing may be statistical processing by means of a publicly-known algorithm concerning outlier removal. More specifically, the statistical processing may be statistical processing by means of an algorithm related to outlier removal through the least median of squares method (LMedS), M estimation method, least squares method (LMS), or Bayesian Filter.

Also in the case of using an algorithm related to outlier removal other than RANSAC, the outlier excluding condition may be provided similarly to RANSAC. For example, when generating the reference spectrum of the fluorochrome A, in the case of excluding a spectrum indicating an outlier from a spectra group obtained from microparticles labeled only with the fluorochrome A, the statistical processing unit 1032 may use an excluding condition based on the shapes of obtained spectra. Accordingly, a spectrum having a shape of low similarity can be excluded.

In addition, in the case of excluding a spectrum indicating an outlier from a spectra group obtained from unstained microparticles, the statistical processing unit 1032 may use an excluding condition based on the intensities of obtained spectra. Accordingly, a spectrum including an abnormal value or a strong noise can be excluded.

Further, in the case of excluding a spectrum indicating an outlier from a spectra group obtained from microparticles labeled only with the fluorochrome A, the statistical processing unit 1032 may further use the excluding condition based on the intensities of obtained spectra. Accordingly, a spectrum having high correlation of spectrum shape but including an abnormal value or the like can be excluded.

The functions of the statistical processing unit 1032 have been described above. Data related to the group of spectra after a spectrum indicating an outlier is excluded by the statistical processing unit 1032 is output to the reference spectrum calculation unit 1033. In addition, the statistical processing unit 1032 may store the data in the storage unit 110. On this occasion, the statistical processing unit 1032 may store the data in the storage unit 110 in association with time information such as the date and time when the data is generated, information related to measured data corresponding to the group of spectra, or the like. In addition, the statistical processing unit 1032 may output the data to the display control unit 120. A screen related to the data is presented to the user by the display control unit 120.

(Reference Spectrum Calculation Unit)

The reference spectrum calculation unit 1033 according to the present embodiment calculates the reference spectrum using the group of spectra from which a spectrum indicating an outlier has been excluded. For example, in the case of calculating the reference spectrum of the fluorochrome A, first, in the statistical processing unit 1032, spectra indicating outliers are excluded from fluorescence spectra (the first spectra group) obtained from microparticles labeled only with the fluorochrome A and autofluorescence spectra (the second spectra group) obtained from unstained microparticles. Next, the reference spectrum calculation unit 1033 calculates the reference spectrum of the fluorochrome A using the first spectra group (the first spectra group after statistical processing) and the second spectra group (the second spectra group after statistical processing) from which spectra indicating outliers have been excluded.

Here, the reference spectrum calculation unit 1033 according to the present embodiment does not perform processing of subtracting a second average spectrum (equivalent to the averaged autofluorescence spectrum) from spectra included in the first spectra group and processing related to normalization of the total sum of the spectra after subtraction as shown in the schematic spectrum F82 and the schematic spectrum F83 in FIG. 8. This is because, in the case where the intensities of spectra included in the first spectra group are weak, the spectrum intensity after subtraction will be negative depending on noises included in the spectra. In the case where the total sum of spectra including negative intensities is normalized, the negative intensities will be further amplified. Accordingly, the accuracy of the reference spectrum obtained by averaging the respective spectra after normalization will be reduced.

The present inventors have studied about a method for improving the problem related to reduction in accuracy as described above. As a result, the present inventors have arrived at reference spectrum calculation processing which will be indicated below.

More specifically, the reference spectrum calculation unit 1033 first calculates the first average spectrum obtained by averaging spectra included in the first spectra group after statistical processing and the second average spectrum obtained by averaging spectra included in the second spectra group after statistical processing. Then, the reference spectrum calculation unit 1033 calculates the reference spectrum by subtracting the second average spectrum from the first average spectrum. Note that averaging stated herein means a simple average of all or part of spectra included in the first spectra group or the second spectra group.

In addition, in this case, the reference spectrum calculation unit 1033 may standardize a spectrum obtained by subtraction to acquire the reference spectrum. Standardization stated herein means normalizing the peak intensity exhibited by the spectrum obtained by subtraction.

By performing the reference spectrum calculation processing following such a procedure, even if a spectrum having a weak intensity is included in the spectra included in the first spectra group, noises included in the spectra are smoothed by averaging. Since the processing related to subtraction of the second average spectrum is performed after this processing related to averaging is performed, a negative intensity is less likely to be included in the reference spectrum obtained after the subtraction processing. Therefore, even if signals related to fluorescence or autofluorescence obtained from microparticles are weak, the accuracy of the reference spectrum obtained is improved.

Note that the reference spectrum calculation unit 1033 according to the present embodiment calculates the reference spectrum by subtracting the second average spectrum from the first average spectrum after calculating the first average spectrum and the second average spectrum, whilst the present technology is not limited to such an example. For example, the reference spectrum calculation unit 1033 may calculate the reference spectrum by subtracting the second average spectrum from each of the spectra included in the first spectra group and averaging the subtracted respective spectra.

In addition, the reference spectrum calculation unit 1033 according to the present embodiment may calculate the second average spectrum obtained by averaging autofluorescence spectra obtained from unstained microparticles included in the second spectra group as the reference spectrum (autofluorescence reference spectrum) related to autofluorescence of microparticles. A spectrum indicating an outlier has already been excluded from the second spectra group by the statistical processing unit 1032. Therefore, the accuracy of the obtained autofluorescence reference spectrum becomes higher than the accuracy of spectra obtained from the second spectra group from which a spectrum indicating an outlier has not been excluded.

Note that calculation of the autofluorescence reference spectrum will also be described in a subsequent second embodiment.

The functions of the reference spectrum calculation unit 1033 have been described above. The reference spectrum calculation unit 1033 may store data related to the calculated reference spectrum in the storage unit 110. On this occasion, the reference spectrum calculation unit 1033 may store the data in the storage unit 110 in association with time information such as the date and time when the data is generated, information related to measured data used for generation of the reference spectrum, or the like. In addition, the reference spectrum calculation unit 1033 may output the data to the display control unit 120. A screen related to the data is presented to the user by the display control unit 120.

For example, the reference spectrum of the fluorochrome A stored in the storage unit 110 is used for analyzing the amount of fluorescence of the fluorochrome A from fluorescence spectra obtained from microparticles labeled with at least one fluorochrome including the fluorochrome A in the amount-of-fluorescence analysis unit 102. In this case, the amount-of-fluorescence analysis unit 102 acquires data related to the reference spectrum of the fluorochrome A stored in the storage unit 110, and uses the reference spectrum for deconvolution of the fluorescence spectra. Accordingly, the amount of fluorescence of the fluorochrome A is analyzed.

2.2. Flow of Processing in Reference Spectrum Generation Unit

Figure 17:
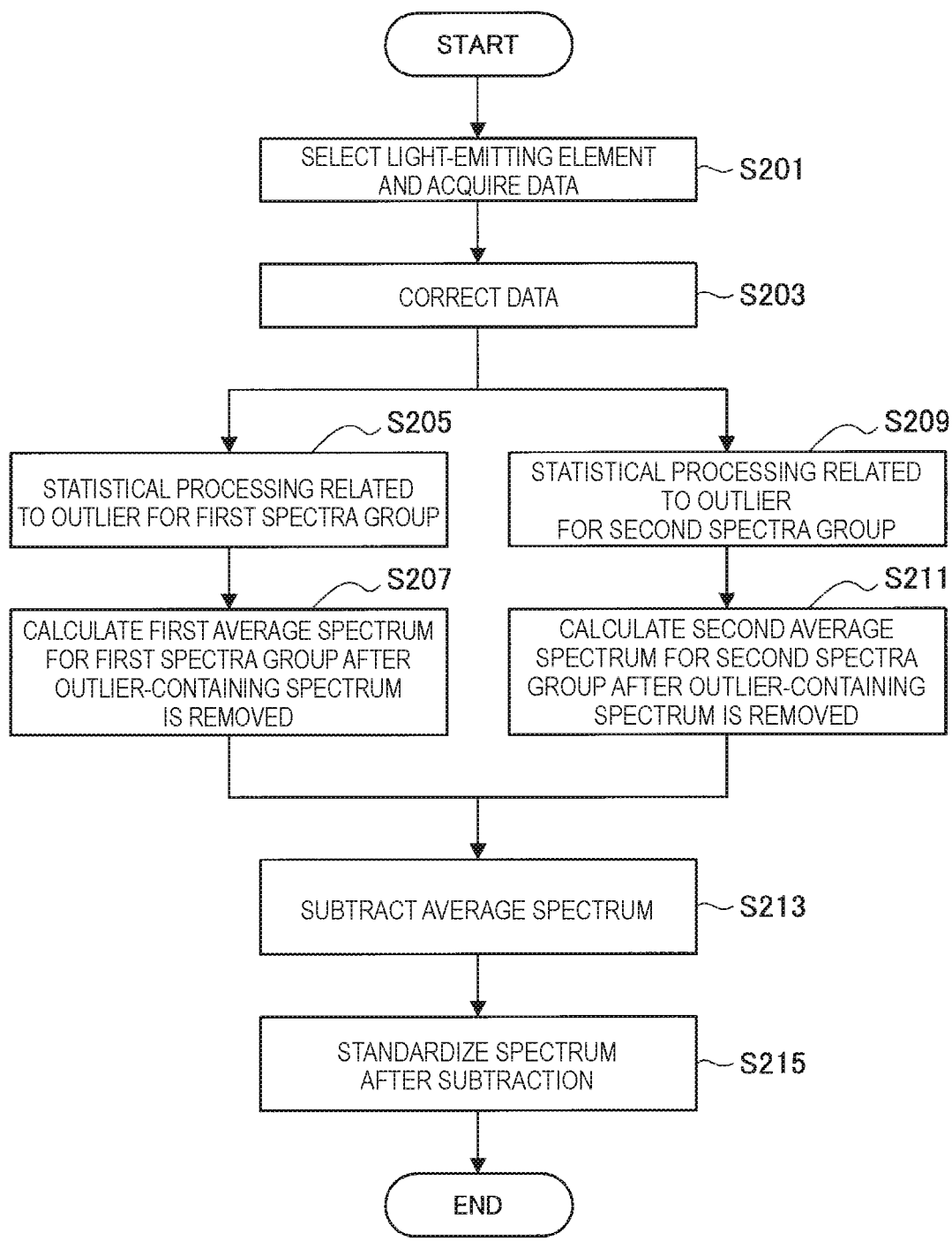
FIG. 17 is a flow chart showing an example of processing performed by the reference spectrum generation unit according to the embodiment.

Next, an example of processing performed by the reference spectrum generation unit 103 according to the first embodiment of the present disclosure will be described with reference to FIG. 17. FIG. 17 is a flowchart showing an example of the processing performed by the reference spectrum generation unit 103 according to the first embodiment of the present disclosure. Here, an example of processing of generating the reference spectrum of the fluorochrome A will be described.

First, the data setting unit 1031 selects a light-emitting element to be a target of generation of the reference spectrum (here, selects the fluorochrome A) (S201). Next, the data setting unit 1031 acquires measured data related to the fluorescence spectrum obtained from microparticles labeled with the fluorochrome A and an autofluorescence spectrum obtained from unstained microparticles from the storage unit 110.

Next, the data setting unit 1031 corrects the acquired measured data (S203). Correction as stated herein may be, for example, correction based on the flowing position of microparticles within the microchannel or correction corresponding to non-uniformity of photoelectric conversion properties in the PMTs.

Then, processing (S205, S207) related to a spectra group (the first spectra group) including spectra related to the fluorochrome A and processing (S209, S211) related to a spectra group (the second spectra group) including autofluorescence spectra, corresponding to the measured data, are performed in parallel. For the first spectra group, the statistical processing unit 1032 first performs statistical processing related to an outlier for the first spectra group, and excludes a spectrum indicating an outlier from the first spectra group (S205). Then, the reference spectrum calculation unit 1033 calculates a simple average spectrum (the first average spectrum) from the first spectra group after the spectrum indicating an outlier is excluded (S207). In addition, for the second spectra group, the statistical processing unit 1032 performs statistical processing related to an outlier for the second spectra group, and excludes a spectrum indicating an outlier from the second spectra group (S209). Then, the reference spectrum calculation unit 1033 calculates a simple average spectrum (the second average spectrum) from the second spectra group after the spectrum indicating an outlier is excluded (S211).

Next, the reference spectrum calculation unit 1033 subtracts the second average spectrum from the first average spectrum, and calculates the reference spectrum before standardization (S213). Then, the reference spectrum calculation unit 1033 standardizes the obtained reference spectrum before the standard (S215). Accordingly, the reference spectrum of the fluorochrome A is generated.

An example of processing performed by the reference spectrum generation unit 103 according to the present embodiment has been described above. Note that, in an example of the processing performed by the above-described reference spectrum generation unit 103, the reference spectrum of the fluorochrome A is generated using measured data related to each of microparticles labeled with the fluorochrome A and unstained microparticles, whilst the present technology is not limited to such an example. For example, the reference spectrum generation unit 103 according to the present embodiment may generate the reference spectrum of the fluorochrome A using measured data related to each of microparticles labeled with a plurality of fluorochromes (for example, the fluorochromes A, B, and C) and microparticles labeled with fluorochromes (for example, the fluorochromes B and C) other than the fluorochrome A. More specifically, the statistical processing unit 1032 may exclude a spectrum indicating an outlier from each of the first spectra group including fluorescence spectra obtained from microparticles labeled with the fluorochromes A, B, and C and the second spectra group including fluorescence spectra obtained from microparticles labeled with the fluorochromes B and C. In this case, the reference spectrum calculation unit 1033 may subtract the average spectrum (the second average spectrum) of the second spectra group after excluding an outlier-containing spectrum from the average spectrum (the first average spectrum) of the first spectra group after excluding an outlier-containing spectrum, and may standardize the spectrum after subtraction. Accordingly, it is possible to obtain the reference spectrum of the fluorochrome A.

2.3. Effects

Figure 18:
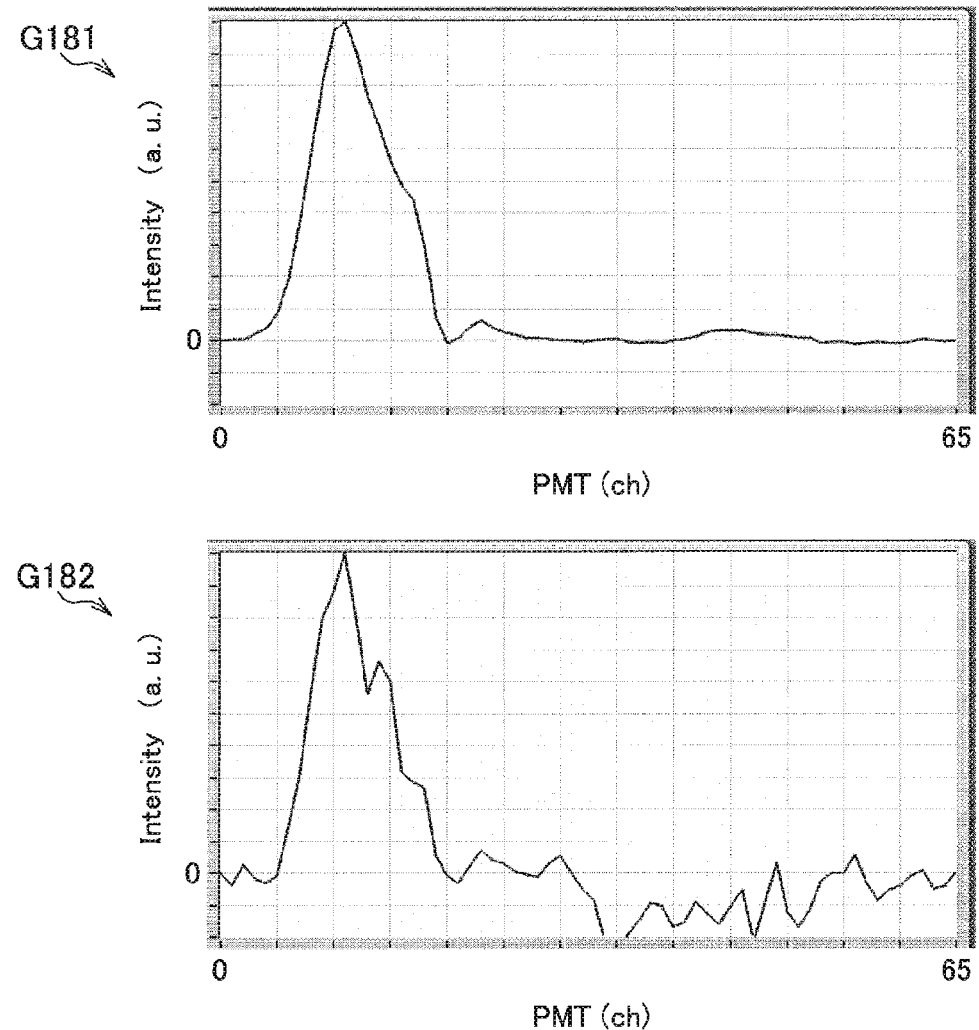
FIG. 18 shows examples of a reference spectrum generated by the processing performed by the reference spectrum generation unit according to the embodiment and a reference spectrum generated by the reference spectrum generation processing shown in FIG. 8.

Next, with reference to FIG. 18, effects obtained by the reference spectrum generation unit 103 according to the present embodiment will be described. FIG. 18 shows examples of a reference spectrum generated by processing performed by the reference spectrum generation unit 103 according to the first embodiment of the present disclosure and a reference spectrum generated by the reference spectrum generation processing shown in FIG. 8. A graph G181 in FIG. 18 is an example of the reference spectrum generated by the processing performed by the reference spectrum generation unit 103 according to the present embodiment. In addition, a graph G182 in FIG. 18 is an example of the reference spectrum generated by the reference spectrum generation processing shown in FIG. 8. Note that the reference spectra shown in FIG. 18 were generated using measured data obtained by performing measurements by the measurement device 20 on lymphocytes labeled with a fluorochrome called AlexaFlour532.

When comparing the reference spectra shown in the graph G181 and the graph G182, it is shown that the reference spectrum generated by the reference spectrum generation unit 103 according to the present embodiment has less noises. This is because a spectrum indicating an outlier has been excluded from a group of spectra in the statistical processing unit 1032. In addition, since standardization by means of the total sum of spectra is not performed in the reference spectrum calculation unit 1033, but standardization is performed after averaging the spectra, wavelength bands having negative intensities hardly exist.

Therefore, with the reference spectrum generation unit 103 according to the present embodiment, a spectrum indicating an outlier can be excluded from a group of spectra. Accordingly, it is possible to prevent measured data indicating an abnormal value, a noise, or the like from being used for the reference spectrum generation processing by means of a measurement condition or the like. Therefore, even if measured data including an abnormal value that occurs irregularly is used in measurements, the accuracy of the reference spectrum generated can be maintained.

In addition, with the reference spectrum generation unit 103 according to the present embodiment, after averaging the group of spectra from which a spectrum indicating an outlier has been excluded, averaged spectra are standardized. Accordingly, many noises that may be included in spectra obtained by weak signals are smoothed. Since spectra standardization processing is performed after this averaging processing, the reference spectrum is less likely to include negative intensities. Therefore, even if signals related to fluorescence or autofluorescence obtained from microparticles are weak, the reference spectrum can be generated with high accuracy.

Note that, in the above-described description, processing of generating the reference spectrum of one fluorochrome has been specifically described using measured data related to fluorescence spectra obtained from microparticles labeled with one fluorochrome and autofluorescence spectra obtained from unstained microparticles, whilst the reference spectrum generation processing according to the present embodiment is not limited to such an example. That is, the above-described generation processing is also applicable to spectra other than fluorescence spectra.

For example, in the case of focusing attention to a mixture in which a plurality of compounds are supposed to have been mixed, the above-described generation processing can be applied to the case of generating the reference spectrum of the compounds using measured data related to emission spectra, absorption spectra, or scattering spectra of the compounds. In this case, the above-described information processing device 10 can perform a quantitative analysis of the compounds included in the mixture using the reference spectra of the compounds generated by the reference spectrum generation unit 103. By applying the above-described generation processing to generation of the reference spectra of the compounds, the accuracy of the quantitative analysis of the compounds included in the mixture can be improved further.

The first embodiment of the present disclosure has been described above.

3. Second Embodiment (Generation of Reference Spectrum Related to Autofluorescence)

Next, the reference spectrum generation unit 103 according to a second embodiment of the present disclosure will be described. The reference spectrum generation unit 103 according to the present embodiment generates a reference spectrum (autofluorescence reference spectrum) related to autofluorescence obtained from unstained microparticles. That is, the reference spectrum generation unit 103 according to the present embodiment not only calculates the reference spectrum of a fluorochrome that labels microparticles, but also can calculate the autofluorescence reference spectrum related to autofluorescence of microparticles.

Note that the configuration of the reference spectrum generation unit 103 and the functional configuration of the information processing device 10 including the reference spectrum generation unit 103 are identical to the functional configuration of the reference spectrum generation unit 103 and the information processing device 10 according to the first embodiment of the present disclosure as shown in FIG. 4 and FIG. 9. Thus, description of the functional configuration about the reference spectrum generation unit 103 will be omitted.

3.1. Flow of Processing in Reference Spectrum Generation Unit

Figure 19:
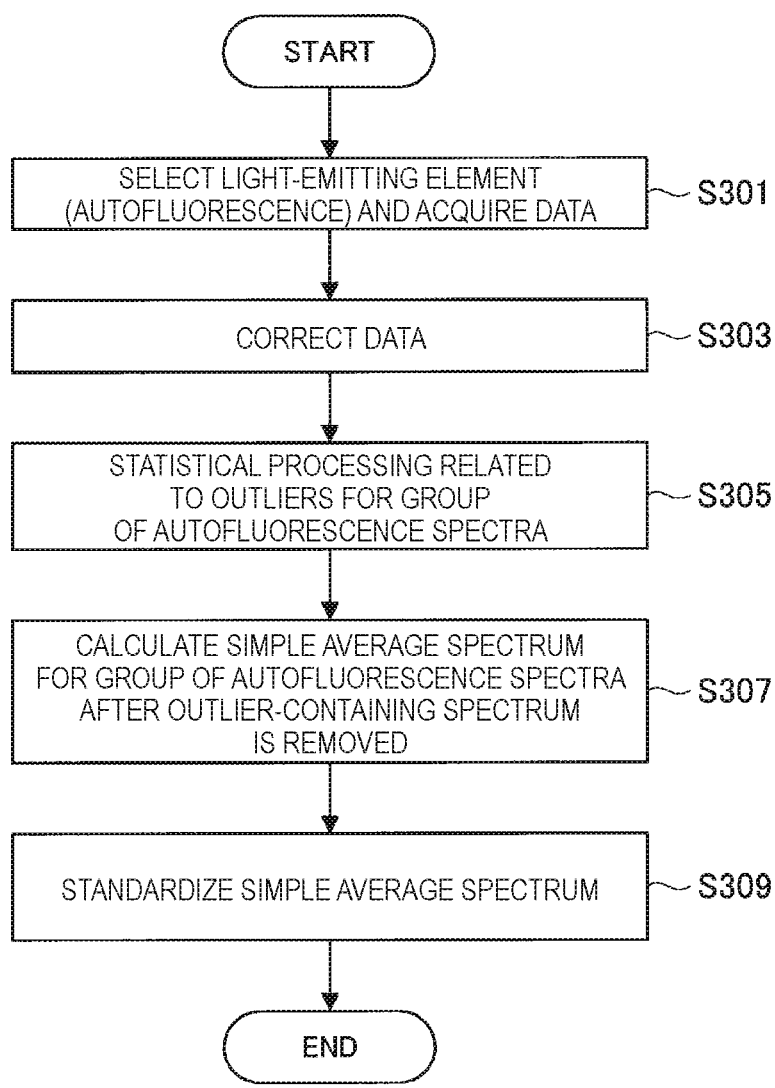
FIG. 19 is a flow chart showing an example of processing performed by a reference spectrum generation unit according to a second embodiment of the present disclosure.

With reference to FIG. 19, an example of processing performed by the reference spectrum generation unit 103 according to the second embodiment of the present disclosure will be described. FIG. 19 is a flowchart showing an example of the processing performed by the reference spectrum generation unit 103 according to the second embodiment of the present disclosure. Here, an example of processing of generating an autofluorescence reference spectrum of one type of microparticles will be described.

First, the data setting unit 1031 selects autofluorescence (for example, Negative in FIG. 10) as a target of generation of the reference spectrum (S301). In addition, the data setting unit 1031 acquires measured data related to autofluorescence spectra obtained from microparticles from the storage unit 110.

Next, the data setting unit 1031 corrects the acquired measured data (S303). Correction as stated herein may be, for example, correction based on the flowing position of microparticles within the microchannel, or correction corresponding to non-uniformity of photoelectric conversion properties in the PMTs.

Then, the statistical processing unit 1032 performs statistical processing related to outliers for a group of autofluorescence spectra related to measured data after correction, and excludes a spectrum indicating an outlier from the autofluorescence spectra (S305). Then, the reference spectrum calculation unit 1033 calculates a simple average spectrum from the group of autofluorescence spectra after the spectrum indicating an outlier is excluded (S307). Then, the reference spectrum calculation unit 1033 standardizes the above-described simple average spectrum (S309). Accordingly, the autofluorescence reference spectrum is generated.

With the reference spectrum generation unit 103 according to the second embodiment of the present disclosure, the autofluorescence reference spectrum related to autofluorescence obtained from one type of microparticles can be generated.

The autofluorescence reference spectrum obtained here is used when sorting a plurality of types of microparticles, for example. Specifically, when sorting a plurality of types of microparticles by flow cytometry, microparticles indicating a spectrum similar to one autofluorescence reference spectrum corresponding to one type of microparticles can be sorted as the one type of microparticles.

3.2. Application Example

Note that, in the autofluorescence reference spectrum generation processing performed by the reference spectrum generation unit 103 according to the present embodiment, it is also possible to perform a cluster analysis for a plurality of pieces of measured data related to a group of unstained microparticles to evaluate the uniformity of the group of microparticles. Hereinafter, an application example of the present embodiment will be described with reference to FIG. 20.

Figure 20:
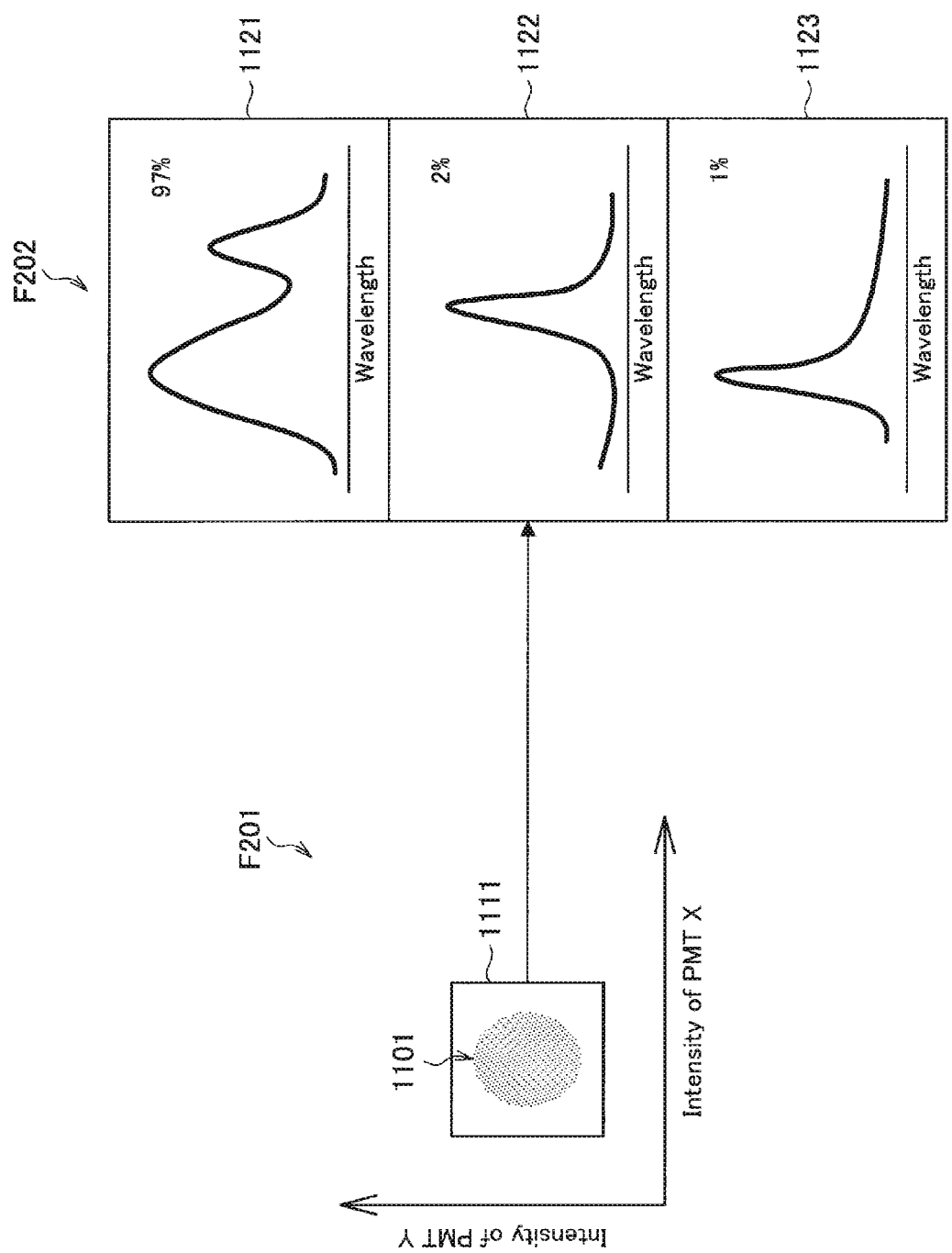
FIG. 20 is a diagram for describing an example of evaluation processing performed by a statistical processing unit according to an application example of the embodiment.

FIG. 20 is a diagram for describing an example of evaluation processing performed by the statistical processing unit 1032 according to the application example of the present embodiment. A schematic view F201 in FIG. 20 is a diagram showing the distribution of fluorescence intensities in specific wavelengths of autofluorescence spectra. A plot 1101 is a plot related to the fluorescence intensities in specific wavelengths of the fluorescence spectra obtained from a group of microparticles. Here, assume that the data setting unit 1031 selects the plot 1101 by a user operation or the like. The selection may be made by setting a frame 1111 so as to enclose the plot 1101 as shown in the schematic view F201, for example. Accordingly, measured data corresponding to the plot enclosed by the frame 1111 is acquired.

Here, the statistical processing unit 1032 performs a cluster analysis for the acquired measured data (a group of autofluorescence spectra). A schematic view F202 of FIG. 20 is a diagram showing an example of the result of the cluster analysis for a plurality of pieces of measured data. Referring to the schematic view F202, it is understood that measured data indicating three types of spectra is included in the measured data having been subjected to the cluster analysis. Specifically, as shown in the schematic view F202, the plurality of pieces of measured data indicate a spectrum 1121 (97%), a spectrum 1122 (2%), and a spectrum 1123 (1%). These spectra may be average spectra or the like of spectra clustered by the cluster analysis. Note that a numeric value shown in each spectrum in the schematic view F202 indicates the proportion occupied by a spectrum similar to any of the spectra 1121 to 1123 among spectra corresponding to the measured data. The proportion shown here is an example of evaluation of uniformity of a group of microparticles.

A group of microparticles measured by the measurement device 20 may include mutants, contamination, or the like. By performing the cluster analysis for measured data related to autofluorescence of the group of microparticles, the uniformity of the group of microparticles can be learned.

In addition, the statistical processing unit 1032 may exclude a spectrum indicating an outlier from a group of autofluorescence spectra using the result of the cluster analysis as shown in the schematic view F202. For example, the statistical processing unit 1032 may exclude spectra clustered into the spectrum 1122 and the spectrum 1123 in the schematic view F202 as spectra indicating outliers. Accordingly, autofluorescence spectra related to microparticles of a type definitely different from one type of microparticles can be prevented from being used for generation of the autofluorescence reference spectrum. Therefore, the accuracy of the autofluorescence spectrum is improved.

In addition, by using the cluster analysis, generation of the autofluorescence reference spectra of a plurality of types of microparticles can be performed at a time. For example, the statistical processing unit 1032 may cluster a plurality of types of autofluorescence spectra by the cluster analysis, and may generate the autofluorescence reference spectrum for each cluster. In addition, by analyzing the amount of fluorescence of autofluorescence of a plurality of types of microparticles again using a plurality of generated autofluorescence reference spectra, it is possible to sort the plurality of types of microparticles.

Note that the cluster analysis shown in the present application example may be a cluster analysis based on a publicly-known algorithm. For example, the cluster analysis may be a cluster analysis based on hierarchical clustering or division optimization clustering such as the k-means method.

In addition, the processing related to the cluster analysis performed by the above-described statistical processing unit 1032 may be performed by the statistical processing unit 1032 according to the above-described first embodiment. In this case, the statistical processing unit 1032 may perform the above-described processing related to the cluster analysis for both of the first spectra group and the second spectra group.

The second embodiment of the present disclosure has been described above.

4. Hardware Configuration Example

Figure 21:
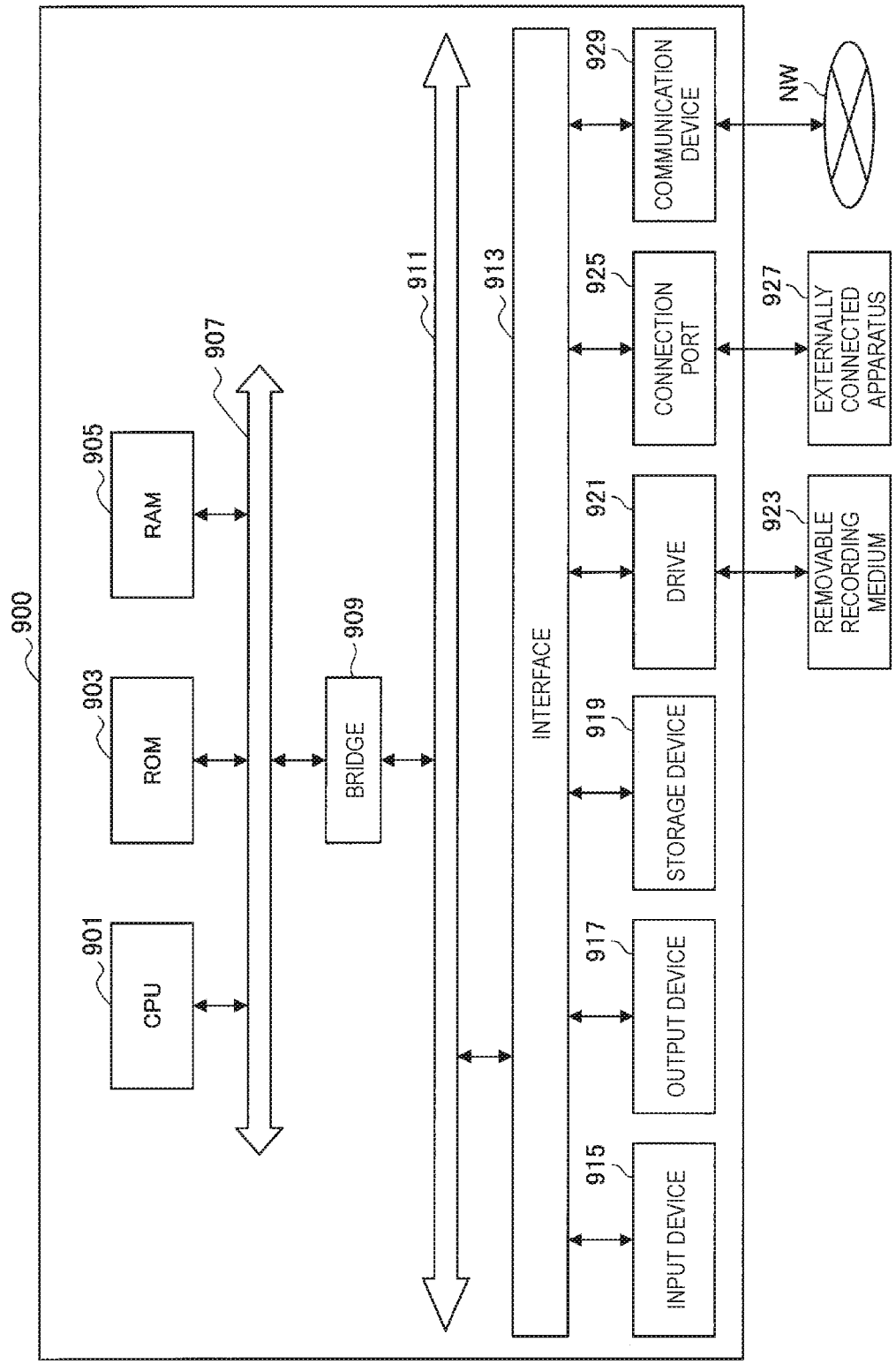
FIG. 21 is a block diagram showing a hardware configuration example of an information processing device according to an embodiment of the present disclosure.

Next, with reference to FIG. 21, a hardware configuration of an information processing device according to an embodiment of the present disclosure is described. FIG. 21 is a block diagram showing a hardware configuration example of the information processing device according to the embodiment of the present disclosure. An illustrated information processing device 900 can realize the information processing device 10 in the above described embodiment.

The information processing device 900 includes a CPU 901, read only memory (ROM) 903, and random access memory (RAM) 905. In addition, the information processing device 900 may include a host bus 907, a bridge 909, an external bus 911, an interface 913, an input device 915, an output device 917, a storage device 919, a drive 921, a connection port 925, and a communication device 929. The information processing device 900 may include a processing circuit such as a digital signal processor (DSP) or an application-specific integrated circuit (ASIC), instead of or in addition to the CPU 901.

The CPU 901 functions as an arithmetic processing device and a control device, and controls the overall operation or a part of the operation of the information processing device 900 according to various programs recorded in the ROM 903, the RAM 905, the storage device 919, or a removable recording medium 923. For example, the CPU 901 controls overall operations of respective function units included in the information processing device 10 of the above-described embodiment. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 927 such as a mobile phone that corresponds to an operation of the information processing device 900. The input device 915 includes an input control circuit that generates input signals on the basis of information which is input by a user to output the generated input signals to the CPU 901. The user inputs various types of data and indicates a processing operation to the information processing device 900 by operating the input device 915.

The output device 917 includes a device that can visually or audibly report acquired information to a user. The output device 917 may be, for example, a display device such as an LCD, a PDP, and an OELD, an audio output device such as a speaker and a headphone, and a printer. The output device 917 outputs a result obtained through a process performed by the information processing device 900, in the form of text or video such as an image, or sounds such as audio sounds.

The storage device 919 is a device for data storage that is an example of a storage unit of the information processing device 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside. Further, the storage device 919 can realize the function of the storage unit 110 according to the above embodiments.

The drive 921 is a reader/writer for the removable recording medium 923 such as a magnetic disk, an optical disc, a magneto-optical disk, and a semiconductor memory, and built in or externally attached to the information processing device 900. The drive 921 reads out information recorded on the mounted removable recording medium 923, and outputs the information to the RAM 905. The drive 921 writes the record into the mounted removable recording medium 923.

The connection port 925 is a port used to directly connect devices to the information processing device 900. The connection port 925 may be a Universal Serial Bus (USB) port, an IEEE1394 port, or a Small Computer System Interface (SCSI) port, for example. The connection port 925 may also be an RS-232C port, an optical audio terminal, a High-Definition Multimedia Interface (HDMI (registered trademark)) port, and so on. The connection of the external connection device 927 to the connection port 925 makes it possible to exchange various kinds of data between the information processing device 900 and the external connection device 927.

The communication device 929 is a communication interface including, for example, a communication device for connection to a communication network NW. The communication device 929 may be, for example, a wired or wireless local area network (LAN), Bluetooth (registered trademark), or a communication card for a wireless USB (WUSB). The communication device 929 may also be, for example, a router for optical communication, a router for asymmetric digital subscriber line (ADSL), or a modem for various types of communication. For example, the communication device 929 transmits and receives signals in the Internet or transits signals to and receives signals from another communication device by using a predetermined protocol such as TCP/IP. The communication network NW to which the communication device 929 connects is a network established through wired or wireless connection. The communication network NW is, for example, the Internet, a home LAN, infrared communication, radio wave communication, or satellite communication.

The example of the hardware configuration of the information processing device 900 has been introduced.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the above-described embodiment has described that the information processing system 1 includes the information processing device 10 and the measurement device 20, whilst the present technology is not limited to such an example. For example, the information processing device 10 may include a function (measuring function) that the measurement device 20 has. In this case, the information processing system 1 is implemented by the information processing device 10. In addition, the measurement device 20 may include functions (data acquiring function, amount-of-fluorescence analyzing function, reference spectrum generating function, and display control function) that the information processing device 10 has. In this case, the information processing system 1 is implemented by the measurement device 20. In addition, the measurement device 20 may have part of the functions that the information processing device 10 has, and the information processing device 10 may have part of the functions that the measurement device 20 has. In addition, the information processing device 10 may only have the function of the reference spectrum generation unit 103. In this case, the other functions such as the amount-of-fluorescence analyzing function may be implemented by another information processing device or the like.

The steps in the processes performed by the information processing device in the present specification may not necessarily be processed chronologically in the orders described in the flowcharts. For example, the steps in the processes performed by the information processing device may be processed in different orders from the orders described in the flowcharts or may be processed in parallel.

Also, a computer program causing hardware such as the CPU, the ROM, and the RAM included in the information processing device to carry out the equivalent functions as the above-described configuration of the information processing device can be generated. Also, a storage medium having the computer program stored therein can be provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

a statistical processing unit configured to perform statistical processing for a group of spectra obtained by applying light to a group of microparticles that exhibit one response property with respect to light, and on a basis of a result of the statistical processing, exclude a spectrum indicating an outlier from the group of spectra; and a reference spectrum calculation unit configured to calculate a reference spectrum using the group of spectra from which the spectrum indicating the outlier has been excluded.

(2)

The information processing device according to (1), in which the statistical processing unit performs statistical processing for each of a first spectra group obtained by applying light to a group of microparticles including one substance that exhibits the one response property and a second spectra group obtained by applying light to a group of microparticles not including the one substance, and on a basis of a result of the statistical processing, excludes spectra indicating outliers from the first spectra group and the second spectra group, respectively, and the reference spectrum calculation unit calculates a reference spectrum related to the one substance using the first spectra group and the second spectra group from which the spectra indicating the outliers have been excluded.

(3)
The information processing device according to (2), in which
the statistical processing unit uses different excluding conditions between processing of excluding a spectrum indicating an outlier from the first spectra group and processing of excluding a spectrum indicating an outlier from the second spectra group.

(4)
The information processing device according to (3), in which
the statistical processing unit
excludes the spectrum indicating the outlier from the first spectra group using an excluding condition based on a spectrum shape, and
excludes the spectrum indicating the outlier from the second spectra group using an excluding condition based on a spectrum intensity.

(5)
The information processing device according to (4), in which
the statistical processing unit excludes the spectrum indicating the outlier from the first spectra group further using the excluding condition based on the spectrum intensity.

(6)
The information processing device according to any one of (2) to (5), in which
the statistical processing unit sets a first reference spectrum and a second reference spectrum corresponding to the first spectra group and the second spectra group, respectively, through the statistical processing, and
excludes the spectra indicating the outliers from the first spectra group and the second spectra group using the first reference spectrum and the second reference spectrum.

(7)
The information processing device according to (6), in which
on a basis of a correlation coefficient between each of spectra included in the first spectra group and the first reference spectrum, the statistical processing unit specifies whether or not each of the spectra included in the first spectra group is a spectrum indicating an outlier.

(8)
The information processing device according to (7), in which
further on a basis of a difference between each of the spectra included in the first spectra group and the first reference spectrum, the statistical processing unit specifies whether or not each of the spectra included in the first spectra group is a spectrum indicating an outlier.

(9)
The information processing device according to (7) or (8), in which
on a basis of a difference between each of spectra included in the second spectra group and the second reference spectrum, the statistical processing unit specifies whether or not each of the spectra included in the second spectra group is a spectrum indicating an outlier.

(10)
The information processing device according to any one of (2) to (9), in which
the reference spectrum calculation unit calculates the reference spectrum by subtracting a second average spectrum obtained by averaging spectra included in the second spectra group from a first average spectrum obtained by averaging spectra included in the first spectra group.

(11)
The information processing device according to (10), in which
the reference spectrum calculation unit calculates the second average spectrum as a reference spectrum related to the group of microparticles not including the one substance.

(12)
The information processing device according to any one of (2) to (11), in which
spectra included in the first spectra group are fluorescence spectra obtained by applying light to simply-stained microparticles stained with one fluorochrome, and
spectra included in the second spectra group are autofluorescence spectra obtained by applying light to unstained microparticles.

(13)
The information processing device according to any one of (1) to (12), in which
the statistical processing unit performs statistical processing for each of a group of autofluorescence spectra obtained by applying light to a group of unstained microparticles, and on a basis of a result of the statistical processing, excludes a spectrum indicating an outlier from the group of autofluorescence spectra, and
the reference spectrum calculation unit calculates an autofluorescence reference spectrum derived from the group of microparticles using the group of autofluorescence spectra from which the spectrum indicating the outlier has been excluded.

(14)
The information processing device according to (13), in which
the statistical processing unit performs a cluster analysis for the group of autofluorescence spectra, and makes an evaluation concerning uniformity of the group of unstained microparticles.

(15)
The information processing device according to (14), in which
on a basis of a result of the evaluation concerning uniformity of the group of unstained microparticles, the statistical processing unit excludes a spectrum indicating an outlier from the group of autofluorescence spectra.

(16)
The information processing device according to any one of (1) to (15), in which
the statistical processing unit makes an evaluation concerning uniformity of the group of spectra on the basis of the result of the statistical processing.

(17)
An information processing method including, by a processor:
performing statistical processing for a group of spectra obtained by applying light to a group of microparticles that exhibit one response property with respect to light, and on a basis of a result of the statistical processing, excluding a spectrum indicating an outlier from the group of spectra; and calculating a reference spectrum using at least one group of spectra from which the spectrum indicating the outlier has been excluded.

(18)

A program for causing a computer to function as:

a statistical processing unit configured to perform statistical processing for a group of spectra obtained by applying light to a group of microparticles that exhibit one response property with respect to light, and on a basis of a result of the statistical processing, exclude a spectrum indicating an outlier from the group of spectra; and a reference spectrum calculation unit configured to calculate a reference spectrum using at least one group of spectra from which the spectrum indicating the outlier has been excluded.

(19)

An information processing system including:

a measurement device including a measurement unit configured to apply light to a measurement target to measure a spectrum related to light emission of the measurement target; and an information processing device including a statistical processing unit configured to perform statistical processing for a group of spectra related to a group of microparticles that exhibit one response property with respect to light, obtained from the measurement unit, and on a basis of a result of the statistical processing, exclude a spectrum indicating an outlier from the group of spectra, and a reference spectrum calculation unit configured to calculate a reference spectrum using at least one group of spectra from which the spectrum indicating the outlier has been excluded.

REFERENCE SIGNS LIST

1 information processing system
10 information processing device
20 measurement device
21 laser light source
22 microchannel
23 photodetector
101 measured data acquisition unit
102 amount-of-fluorescence analysis unit
103 reference spectrum generation unit
110 storage unit
120 display control unit
230 detector
231 PMT
232 dichroic mirror
1031 data setting unit
1032 statistical processing unit
1033 reference spectrum calculation unit

The invention claimed is:

1. An information processing device, comprising:
a processor configured to:
execute a statistical process for each of a first spectra group and a second spectra group, wherein
the first spectra group is obtained by application of light to a first group of microparticles,
the first group of microparticles includes a substance that exhibits a response property with respect to the light,
the second spectra group is obtained by the application of the light to a second group of microparticles, and
the substance is absent in the second group of microparticles;
exclude each of:
a first spectrum, indicating a first outlier, from the first spectra group, and
a second spectrum, indicating a second outlier, from the second spectra group,
wherein each of the exclusion of the first spectrum from the first spectra group and the exclusion of the second spectrum from the second spectra group is based on a result of the execution of the statistical process; and
calculate a first reference spectrum, related to the substance, based on:
the first spectra group from which the first spectrum is excluded, and
the second spectra group from which the second spectrum is excluded.

2. The information processing device according to claim 1, wherein the processor is further configured to:
exclude the first spectrum indicating the first outlier from the first spectra group based on a first excluding condition; and
exclude the second spectrum indicating the second outlier from the second spectra group based on a second excluding condition different from the first excluding condition.

3. The information processing device according to claim 2, wherein
the first excluding condition is based on a spectrum shape, and
the second excluding condition is based on a spectrum intensity.

4. The information processing device according to claim 3, wherein the processor is further configured to exclude the first spectrum indicating the first outlier from the first spectra group based on the second excluding condition.

5. The information processing device according to claim 1, wherein the processor is further configured to:
set a second reference spectrum corresponding to the first spectra group based on the execution of the statistical process;
set a third reference spectrum corresponding to the second spectra group based on the execution of the statistical process;
exclude the first spectrum indicating the first outlier from the first spectra group based on the second reference spectrum; and
exclude the second spectrum indicating the second outlier from the second spectra group based on the third reference spectrum.

6. The information processing device according to claim 5, wherein the processor is further configured to specify whether each spectrum of the first spectra group indicates the first outlier, based on a correlation coefficient between each spectrum of the first spectra group and the second reference spectrum.

7. The information processing device according to claim 6, wherein the processor is further configured to specify, whether each spectrum of the first spectra group indicates the first outlier, based on a difference between each spectrum of the first spectra group and the second reference spectrum.

8. The information processing device according to claim 5, wherein the processor is further configured to specify, whether each spectrum of the second spectra group indicates the second outlier, based on a difference between each spectrum of the second spectra group and the third reference spectrum.

9. The information processing device according to claim 1, wherein the processor is further configured to:
   determine a first average spectrum based on an average of spectra in the first spectra group;
   determine a second average spectrum based on an average of spectra in the second spectra group; and
   calculate the first reference spectrum by subtraction of the second average spectrum from the first average spectrum.

10. The information processing device according to claim 9, wherein the second average spectrum is related to the second group of microparticles not including the substance.

11. The information processing device according to claim 1, wherein
   the first spectra group includes fluorescence spectra,
   the first group of microparticles are simply-stained microparticles stained with at least one fluorochrome,
   the second spectra group includes autofluorescence spectra, and
   the second group of microparticles are unstained microparticles.

12. The information processing device according to claim 11, wherein the processor is further configured to:
   execute a cluster analysis for the autofluorescence spectra, and
   evaluate uniformity of the unstained microparticles.

13. The information processing device according to claim 12, wherein the processor is further configured to exclude the second spectrum indicating the second outlier from the autofluorescence spectra based on a result of the evaluation of the uniformity of the unstained microparticles.

14. The information processing device according to claim 1, wherein the processor is further configured to evaluate uniformity of each of the first spectra group and the second spectra group based on the result of the execution of the statistical process.

15. An information processing method, comprising:
   executing a statistical process for each of a first spectra group and a second spectra group, wherein
      the first spectra group is obtained by application of light to a first group of microparticles,
      the first group of microparticles includes a substance that exhibits a response property with respect to the light,
      the second spectra group is obtained by the application of the light to a second group of microparticles, and
      the substance is absent in the second group of microparticles;
   excluding each of:
      a first spectrum, indicating a first outlier from the first spectra group, and
      a second spectrum, indicating a second outlier, from the second spectra group,
      wherein each of the exclusion of the first spectrum from the first spectra group and the exclusion of the second spectrum from the second spectra group is based on a result of the execution of the statistical process; and
   calculating a reference spectrum, related to the substance, based on:
      the first spectra group from which the first spectrum is excluded, and
      the second spectra group from which the second spectrum is excluded.

16. A non-transitory computer-readable medium having stored thereon, computer-executable instructions which, when executed by a processor, cause the processor to execute operations, the operations comprising:
   executing a statistical process for each of a first spectra group and a second spectra group, wherein
      the first spectra group is obtained by application of light to a first group of microparticles,
      the first group of microparticles includes a substance that exhibits a response property with respect to the light,
      the second spectra group is obtained by the application of the light to a second group of microparticles, and
      the substance is absent in the second group of microparticles;
   excluding each of:
      a first spectrum, indicating a first outlier, from the first spectra group, and
      a second spectrum, indicating a second outlier, from the second spectra group,
      wherein each of the exclusion of the first spectrum from the first spectra group and the exclusion of the second spectrum from the second spectra group is based on a result of the execution of the statistical process; and
   calculating a reference spectrum, related to the substance, based on:
      the first spectra group from which the first spectrum is excluded, and
      the second spectra group from which the second spectrum is excluded.

17. An information processing system, comprising:
   a measurement device configured to:
      apply light to each of a first group of microparticles and a second group of microparticles, wherein
         the first group of microparticles includes a substance that exhibits a response property with respect to the light, and
         the substance is absent in the second group of microparticles;
      measure a first spectra group related to emission of the light from the first group of microparticles, wherein the emission of the light from the first group of microparticles is based on the application of the light to the first group of microparticles; and
      measure a second spectra group related to emission of the light from the second group of microparticles, wherein the emission of the light from the second group of microparticles is based on the application of the light to the second group of microparticles; and
   an information processing device including a processor, wherein the processor is configured to:
      acquire first measurement data and second measurement data from the measurement device, wherein
         the first measurement data is a result of the measurement of the first spectra group, and
         the second measurement data is a result of the measurement of the second spectra group;
      execute a statistical process for each of the first spectra group and the second spectra group based on the acquired first measurement data and the second measurement data;
      exclude each of:
         a first spectrum, indicating a first outlier, from the first spectra group, and a second spectrum, indicating a second outlier, from the second spectra group,
wherein each of the exclusion of the first spectrum from the first spectra group and the exclusion of the second spectrum from the second spectra group is based on a result of the execution of the statistical process; and calculate a reference spectrum, related to the substance, based on:
the first spectra group from which the first spectrum is excluded, and
the second spectra group from which the second spectrum is excluded.

\* \* \* \* \*